US012590170B2

(12) United States Patent
Puzer et al.

(10) Patent No.: US 12,590,170 B2
(45) Date of Patent: Mar. 31, 2026

(54) RECOMBINANT HUMAN ANTIBODIES THAT INHIBIT THE HUMAN TISSUE KALLIKREIN 7 (KLK7) AND THEIR USE AGAINST DISEASES THAT CAUSE DESQUAMATION OF THE SKIN

(71) Applicants:Fundação Universidade Federal do ABC—UFABC, Santo André (BR); Technische Universität Braunschweig, Braunschweig (DE)

(72) Inventors: Luciano Puzer, São Paulo (BR); Ana Flávia Santarine Laureano, Santo André (BR); Daniele Ribeiro De Araújo, Santo André (BR); Michael Hust, Braunschweig (DE)

(73) Assignees: Fundação Universidade Federal do ABC—UFABC, Santo André (BR); Technische Universität Braunschweig, Braunschweig (DE)

( * ) Notice: Subject to any disclaimer, the term of this patent is extended or adjusted under 35 U.S.C. 154(b) by 673 days.

(21) Appl. No.: 17/925,061

(22) PCT Filed: May 14, 2021

(86) PCT No.: PCT/BR2021/050201
§ 371 (c)(1),
(2) Date: Nov. 14, 2022

(87) PCT Pub. No.: WO2021/226695
PCT Pub. Date: Nov. 18, 2021

(65) Prior Publication Data
US 2023/0183375 A1 Jun. 15, 2023

(30) Foreign Application Priority Data
May 14, 2020 (BR) ........................ 10 2020 0096796

(51) Int. Cl.
| | |
|---|---|
| *C07K 16/40* | (2006.01) |
| *A61K 9/00* | (2006.01) |
| *A61K 9/06* | (2006.01) |
| *A61K 47/34* | (2017.01) |
| *A61K 39/00* | (2006.01) |

(52) U.S. Cl.
CPC ............ *C07K 16/40* (2013.01); *A61K 9/0014* (2013.01); *A61K 9/06* (2013.01); *A61K 47/34* (2013.01); *A61K 2039/54* (2013.01); *C07K 2317/622* (2013.01); *C07K 2317/92* (2013.01)

(58) Field of Classification Search
CPC ........ C07K 16/40; A61K 9/0014; A61K 9/06; A61K 47/34
See application file for complete search history.

(56) References Cited

U.S. PATENT DOCUMENTS

| | | |
|---|---|---|
| 5,834,290 A | 11/1998 | Egclrud |
| 10,472,423 B2 | 11/2019 | Wang |

FOREIGN PATENT DOCUMENTS

| | | |
|---|---|---|
| BR | 102014027271 | 7/2018 |
| RU | 2738802 | 12/2020 |
| WO | WO 2021/055577 | 3/2021 |

OTHER PUBLICATIONS

Bedouelle, et al. Diversity and junction residues at hotspots of binding energy in an antibody neutralizing the dengue virus. FEBS J. Jan. 2006; 273(1):34-46.*

Meyer, et al. New insights in type I and II CD20 antibody mechanisms-of-action with a panel of novel CD20 antibodies. British Journal of Haematology. 2018. 180:808-820.*

Vajdos, et al. Comprehensive functional maps of the antigen-binding site of an anti-ErbB2 antibody obtained with shotgun scanning mutagenesis. Journal of Molecular Biology. 2002. 320(2):415-28.*

Morizane S et al. "TH2 cytokines increase kallikrein 7 expression and function in patients with atopic dermatitis." Journal of Allergy and Clinical Immunology 130: 259-261. (Year: 2012).*

Komatsu N et al. "Aberrant human tissue kallikrein levels in the stratum corneum and serum of patients with psoriasis: dependence on phenotype, severity and therapy." British Journal of Dermatology 156: 875-883. (Year: 2007).*

Kasparek P et al. "KLK5 and KLK7 Ablation Fully Rescues Lethality of Netherton Syndrome-Like Phenotype." PLOS Genetics 13: e1006566. (Year: 2017).*

International Search Report and the Written Opinion Dated Aug. 30, 2021 From the International Searching Authority Re. Application No. PCT/BR2021/050201 and itst Translation into English. (26 Pages).

Laureano et al. "Generation of Recombinant Antibodies Against Human Tissue Kallikrein 7 to Treat Skin Diseases", Bioorganic & Medicinal Chemistry Letters, 30(23): 127626-1-127626-10, Published Online Oct. 20, 2020.

Laureano et al. "Generation of Soluble Antibodies Against Human Tissue Kallikrein 7 and the Evaluation of Their Biopharmaceutical Use With A Poloxamer-Based Hydrogel Drug Delivery System", Authorca, p. 1-12, Dec. 17, 2019.

Laureano et al. "Polymeric Hydrogels as A Drug Delivery System for Anti-Human KLK7 Recombinant Antibodies", XLVII Reunião Anual da Sociedade Brasileira de Bioquímica e Biologia Molecular 2018 [47th Annual Meeting of the Brazilian Society for Biochemistry and Molecular Biology (SBBq)], Joinville, SC, Brazil, May 26-29, 2018, H—Mechanisms of Drug Action, p. 200: #H-36, May 26, 2018.

(Continued)

*Primary Examiner* — Anne M. Gussow

(57) ABSTRACT

The present invention relates to human tissue kallikrein 7 (KLK7) selective inhibitor compounds, combinations including these compounds, process to obtain the referred compounds, and methods of using the same. The present invention belongs to the field of chemistry, pharmacology and medicine.

15 Claims, 5 Drawing Sheets

Specification includes a Sequence Listing.

(56) References Cited

OTHER PUBLICATIONS

Supplementary European Search Report and the European Search Opinion Dated Aug. 28, 2024 From the European Patent Office Re. Application No. 21802991.6. (13 Pages).

Kügler et al. "Construction of Human Immune and Naive ScFv Libraries", Phage Display: Methods and Protocols, Methods in Molecular Biology, XP093192066, Protocols for In Vitro Cultures and Scondary Metabolite Analysis of Aromatic and Medicinal Plants, 2nd Ed., Chap.1: 1-22, Jan. 1, 2018.

Kügler et al. "Generation and Analysis of the Improved Human HAL9/10 Antibody Phage Display Libraries", BMC Biotechnology, XP021213967, 15(1): 10-1-10-15, Feb. 19, 2015.

Laureano Santarine "Seleção de Anticorpos Recombinantes (ScFv-Fc) Anti-KLK7 Humana e Caracterização de Um Sistema de Hidrogel Polimérico Para Drug Delivery Na Pele", Sistema de Biobliotecas da UFAB, XP093192094, 1 P., Feb. 11, 2020.

R&D Systems "Human Kallikrein 7 Antibody: Monoclonal Mouse IgG2A; Clone #333931", R&D Systems, A Biotechne Brand, XP055756013, Catalog No. MAB2624, 1 P., Feb. 7, 2018.

UFABC "PPGBTC Pós-Graduaço Em Biotecociência", Portal de Programas de Pós-Graduação (UFABC), XP093192091, p. 1-13, Aug. 2, 2024.

* cited by examiner

| Clone | IC₅₀ (nM) |
|---|---|
| LUP-14B12 | 275.0 |
| LUP-14C4 | 365.5 |
| LUP-14D6 | 79.9 |
| LUP-14E9 | 420.0 |
| LUP-14E12 | 273.0 |
| LUP-14F7 | 151.5 |
| LUP-14F10 | 18.9 |
| LUP-14G8 | 100.8 |
| LUP-14G10 | 2.3 |

1

RECOMBINANT HUMAN ANTIBODIES THAT INHIBIT THE HUMAN TISSUE KALLIKREIN 7 (KLK7) AND THEIR USE AGAINST DISEASES THAT CAUSE DESQUAMATION OF THE SKIN

RELATED APPLICATIONS

This application is a National Phase of PCT Patent Application No. PCT/BR2021/050201 having International filing date of May 14, 2021, which claims the benefit of priority of Brazil Patent Application No. BR 10 2020 009679 6 filed on May 14, 2020. The contents of the above applications are all incorporated by reference as if fully set forth herein in their entirety.

SEQUENCE LISTING STATEMENT

The ASCII file, entitled 94707SequenceListing.txt, created on Nov. 14, 2022, comprising 72,246 bytes, submitted concurrently with the filing of this application is incorporated herein by reference. The sequence listing submitted herewith is identical to the sequence listing forming part of the international application.

FIELD AND BACKGROUND OF THE INVENTION

The present invention relates to antibodies and their fragments, specific to inhibit the proteolytic activity of the of human tissue kallikrein 7 (KLK7), besides the formulations that include the referred antibodies, encapsulated in polymeric hydrogels, to be applied directly to the skin. The present invention also relates to the process to obtain the referred antibodies and their fragments, formulations containing the antibodies and their fragments, and their use in medical treatment of skin diseases.

Human tissue kallikreins are a group of fifteen serine proteases (KLK1-KLK15) expressed in many tissues of the human body (DIAMANDIS et al., Clin. Chem., 2000.; SOTIROPOULOU et al., J. Biol. Chem., 2009). The kallikreins family caught much attention in the past few years by the fact that kallikreins are expressed differently in normal tissues when compared with carcinogenic tissues, which has proven to be useful for monitoring and diagnosis of certain carcinomas. The most diffused example is KLK3 (or PSA) which is considered the most powerful biomarker for prostate cancer (CATALONA et al., New Engl. J. Med., 1991; OESTERLING et al., J. Urol., 1991). Kallikreins altered expression is related with several pathologies: respiratory diseases, neurodegenerative diseases and, as described before, skin diseases and hormone-related cancers. These enzymes became attractive targets for therapeutics (FILIPPOU, Clin. Proteom., 2017).

Literature reports point out the participation of KLKs 5 and 7 in epidermal homeostasis, notably in the process of desquamation of the skin, which is important for the continuous regeneration of the epithelial tissue (EKHOLM; BRATTSAND; EGELRUD, J. Invest. Dermatol., 2000). These enzymes are responsible for the cleavage of the corneodesmosomes, which are protein structures responsible for the cellular cohesion (LUNDWALL; BRATTSAND, Biol. Chem., 2008).

In the deepest layers of the skin these enzymes are found in the form of pro-enzymes and do not present catalytic activity. Furthermore, high concentrations of Zn' and LEKTI (Kazal-Type KLK Inhibitor) regulate the activity after activation. As cells migrate towards the superficial layers of the skin, the zinc concentration reduces in conjunction with pH, LEKTI dissociates from KLKs, which become active (by autolysis or proteolysis of other enzymes), promoting degradation of corneodesmosomes and, hence, desquamation of the skin (LUNDWALL & BRATTSAND, Cell. Mol. Life Sci., 2008).

KLK7 is the only enzyme with chymotrypsin mode of action in the epidermis and it is actively involved in the skin desquamation process (DIAMANDIS & YOUSEF, Expert Rev. Mol. Diagn., 2001); it is secreted by lamellar granules directly in the intracellular space, between the *stratum granulosum* and *stratum corneum*, where directly cleavages desmocollin-1 and corneodesmosin (ISHIDA-YAMA-MOTO et al., J. Invest. Dermatol., 2004). It was demonstrated that KLK7 has increased activity in dermatological pathologies as atopic dermatitis (VOEGELI et al., Int. J. Cosmetic Sci., 2011), psoriasis (KOMATSU et al., J. Invest. Dermatol., 2006) and Netherton syndrome (KOMATSU et al., J. Invest. Dermatol., 2008). Several literature reviews point out the potential use of kallikreins as therapeutic targets for these dermatological disorders (AVGERIS et al., Biol. Chem., 2012; PRASSAS et al., Nat. Rev. Drug. Discov., 2015; MASURIER et al., Med. Res. Rev., 2018; SOUALMIA & EL AMRI, 2018).

In this line of drugs for dermatological diseases, the French startup Dermadis (www (dot) dermadis (dot) com) has the patent for DM107 compound, which has the capability to inhibit kallikreins. This compound is in the last phase of preclinical testing, and should briefly be used in clinical trials in humans aiming to control the Netherton syndrome. It is expected that this drug could also be used against psoriasis and atopic dermatitis. However, this compound is based on peptide sequences. Peptide sequences are subjected to rapid metabolization, besides presenting great risk of immunological response.

Antibodies have several properties that make them the perfect starting point for the search of new biopharmaceuticals. They occur naturally and at large concentrations in the organism, besides having a long half-life time. They are extremely specific and have inherent effector functions. These functions are located in different protein domains within the Ig molecule structure and can be genetically modified, aiming to improve the affinity and specificity between an antibody and its antigen, thus creating a wide range of new molecules with enormous therapeutic potential (ADAIR, Biotechnol., 1999). Besides therapeutic uses, antibodies are used in research and as diagnostic tools. They are also used in tests such as immunoblotting, flow cytometry and immunohistochemistry (FRENZEL et al., Front. Immunol., 2013).

Recombinant antibodies represent, on the market, the most important class of recombinant proteins for therapeutic use. In May 2016 more than 50 antibodies and antibody-drug conjugates were approved by FDA (Food and Drug Administration) in the United States and by EMA (European Medicines Agency) in Europe. There are still about 500 molecules under investigation (CAI, MOJ Immunol., 2017).

The search in the patent literature pointed out some relevant documents that will be described below.

Patent WO2013010963A1 describes the use of coumarin-derived molecules for the treatment of dermatological diseases.

Patent US20170065570A1 describes aromatic compounds used for inhibition of KLK7 in skin diseases.

Patent WO2012083385A1 describes a molecule targeted to inhibit the activity of KLKs 5, 7 and 14, consisting of a peptide compound.

Patent CN106518880A describes a KLK7-inhibiting peptide molecule, as well as its synthesis.

Patent WO2016044662A1 describes pyridone compounds as serine protease inhibitors, that exhibit inhibitory action against thrombin and various kallikreins.

Patent WO2015112081A1 describes benzoxazin molecules for inhibition of kallikreins 5, 7 and 14.

It is clear, from the literature review, that there are several molecules designed for the inhibition of kallikreins, but they are organic molecules. There are no documents in the state of the art anticipating or suggesting the existence of antibodies or fragments of antibodies, or their fragments, specific to the inhibition of KLK7, requiring compounds adequately effective to inhibit KLK7.

SUMMARY OF THE INVENTION

In a first aspect, the present invention relates to an antibody, or fragment thereof, comprising an amino acid sequence having at least 80% similarity to any one of SEQ ID #2, 4, 6, 8, 10, 12, 14, 16, 18, 20, 22, 24 or 26.

In one embodiment, the antibody, or fragment thereof, comprises an amino acid sequence as described in any one of SEQ ID #2, 4, 6, 8, 10, 12, 14, 16, 18, 20, 22, 24 or 26.

In another preferred embodiment, the antibody, or fragment thereof, consists of the amino acid sequence as described in any one of SEQ ID #2, 4, 6, 8, 10, 12, 14, 16, 18, 20, 22, 24 or 26.

In another embodiment, the antibody, or fragment thereof, is an scFv, scFv-Fc or IgG antibody.

In an even more preferred embodiment, the antibody, or fragment thereof, is a scFv antibody.

In a second aspect, the invention relates to a nucleotide sequence that encodes an antibody, or fragment thereof, according to the first aspect of the invention.

In one embodiment, the nucleotide sequence comprises a nucleic acid sequence with at least 80% similarity to any one of SEQ ID #1, 3, 5, 7, 9, 11, 13, 15, 17, 19, 21, 23 and 25.

In another embodiment, the nucleotide sequence comprises a nucleic acid sequence as described in any one of SEQ ID #1, 3, 5, 7, 9, 11, 13, 15, 17, 19, 21, 23 and 25.

In a preferred embodiment, the nucleotide sequence consists of the nucleic acid sequence as described in any one of SEQ ID #1, 3, 5, 7, 9, 11, 13, 15, 17, 19, 21, 23 and 25.

In a third aspect, the invention relates to a composition comprising an antibody, or fragment thereof, according to an aspect of the present invention.

In one embodiment, the composition is formulated for topical use.

In another embodiment, the composition is in the form of a suspension, emulsion, spray lotion, unguent, cream, gel, plaster, film, ointment, or incorporated into patches.

In a preferred embodiment, the composition is in the form of a gel, lotion, cream or ointment.

In an even more preferred embodiment, the composition is in the form of a hydrogel.

In an even further preferred embodiment, the gel according to the present invention is a poloxamer-based hydrogel.

In another preferred embodiment, the poloxamer is poloxamer 407 and/or poloxamer 403.

In another embodiment, the composition is for use as a medication.

In another aspect, the invention relates to the use of an antibody, or fragment thereof, according to one aspect of the invention, or a composition according to another aspect of the invention, for the manufacture of a medication for the treatment or prevention of diseases or disorders related to KLK7.

In one embodiment, the diseases or disorders related to KLK7 are due to KLK7 increased activity.

In a preferred embodiment, the disease or disorder is a dermatological pathology.

In another preferred embodiment, the dermatological pathology is selected among atopic dermatitis, psoriasis and Netherton syndrome.

In a last aspect, the invention relates to a method of treating or preventing KLK7-related diseases or disorders, by administering an antibody, or fragment thereof, according to an aspect of the invention, or a composition according to another aspect of the invention, to an individual in need thereof.

In one embodiment, the KLK7-related diseases or disorders are due to KLK7 increased activity.

In a preferred embodiment, the disease or disorder is a dermatological pathology.

In another preferred embodiment, the dermatological pathology is selected among atopic dermatitis, psoriasis and Netherton syndrome.

DESCRIPTION OF SPECIFIC EMBODIMENTS OF THE INVENTION

Figure 1:
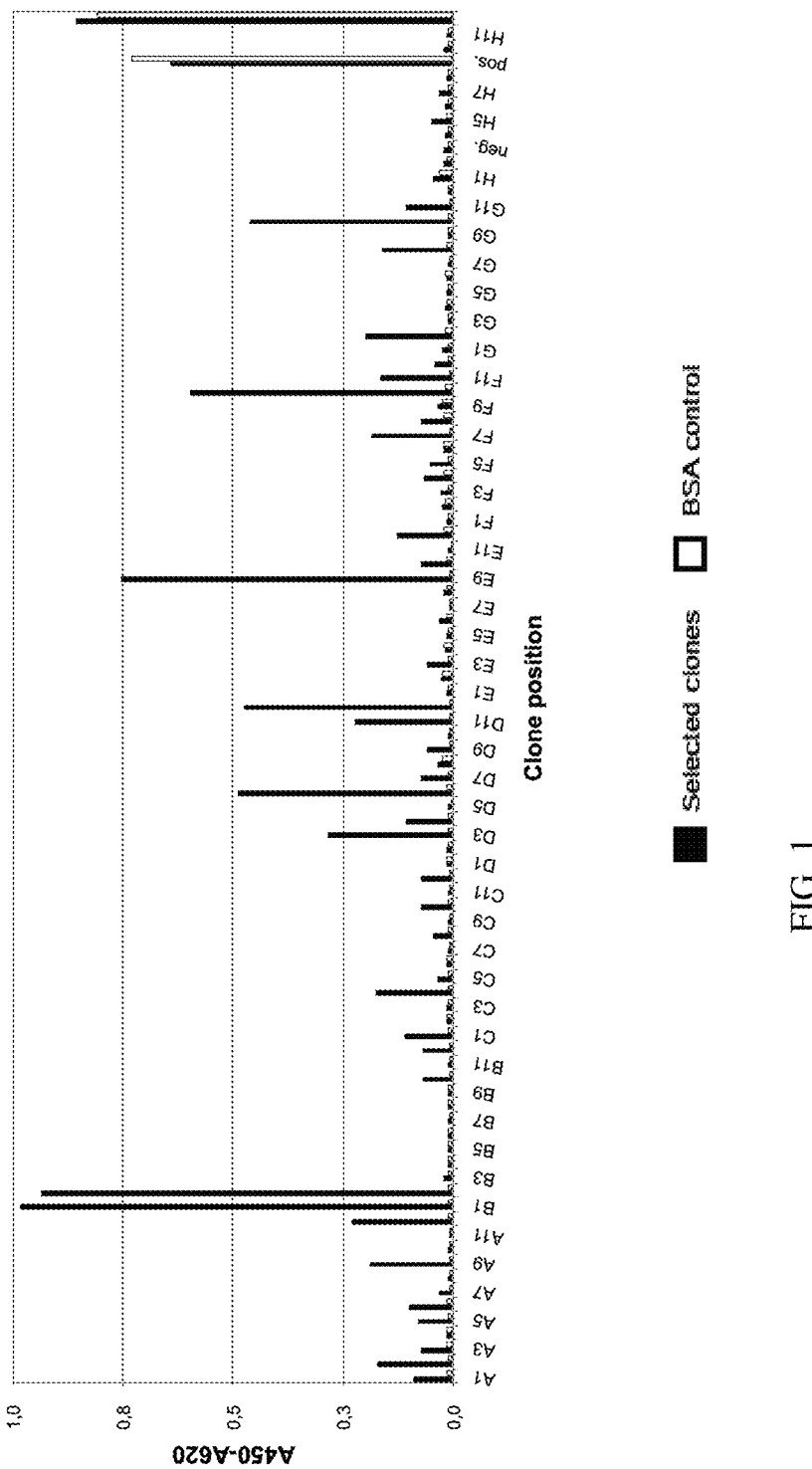
FIG. 1: scFv antibodies selected against KLK7 from the HAL9/10 library. The dark bars represent the selected clones, the empty bars represent the negative control made with BSA, the positive (lysozyme) and negative (empty wells) are marked at the X axis as "pos" and "neg", respectively.
Figure 2:
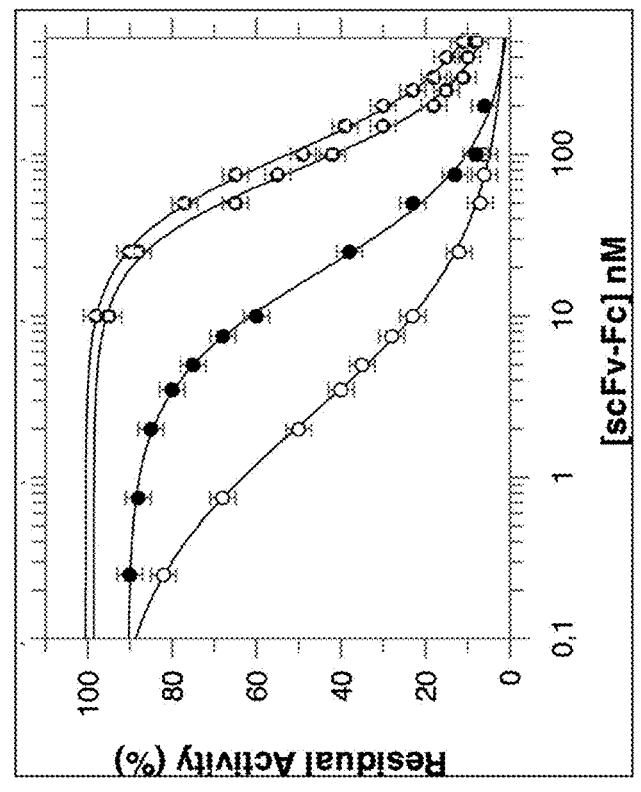
FIG. 2: IC50 of antibodies selected against KLK7 from the naïve library HAL9/10. In the graph, triangles represent LUP-14G8, squares LUP-14D6, dark circles LUP-14F10 and empty circles LUP-14G10.

Unless otherwise defined, all technical and scientific terms used herein have the same meaning as understood by one skilled in the art to which the invention falls. Conventional molecular biology and immunology techniques are well known to one skilled in the art. The specification also provides definitions of terms to aid in the interpretation of what is described herein and in the claims. Unless otherwise stated, all figures expressing amounts, percentages and proportions, and other numerical values used in the specification and claims, are to be understood as being impaired, in all cases, by the term "around". Thus, unless otherwise stated, the numerical parameters shown in the specification and in the claims are approximations that may vary depending on the properties to be obtained.

As used herein, the term "Antibody" is to be understood in its broad meaning. An antibody is an immunoglobulin molecule that has the ability to specifically bind to a antigen in particular. Antibodies are well known to one skilled in the art. An antibody includes, but it is not limited to, a traditional antibody, a fragment of a traditional antibody containing an antigen-binding site, a scFv fragment, a recombinant antibody containing an antigen-binding site, a protein that binds to an antigen, and a product comprising a link between two or among more of these.

An antibody can be in its pure form or in a mixture. An antibody may be in a modified form (e.g., chemically modified) or it may be in an unmodified form.

According to the present invention, the antibodies of interest can be generated by means of the phage display technique. Antibody phage display technology is a key technology enabling the generation of human antibodies for diagnosis and therapy.

For the generation of human antibodies by phage display, according to the present invention, two types of antibody gene libraries can be used: immunological libraries and universal or "single-pot" libraries.

Immunological libraries of patients are suitable for selecting specific antibodies against a disease or pathogen, e.g., cancer, human immunodeficiency virus or herpes simplex virus. On the other hand, "single-pot" libraries theoretically allow selection of antibodies against any target.

Preferably, in accordance with the present invention, human naïve antibody gene libraries are used, such as the McCafferty library, the Pfizer library, the Tomlinson libraries or the Human/Hust (HAL) 4/7/8 and 9/10 antibody libraries. Preferably, HAL4/7/8 or 9/10 libraries are used. In an even more prefential manner, the antibodies, according to the present invention, are generated from HAL9/10 phage libraries.

The antibody fragments from these libraries can be directly cloned into a selection of compatible expression vectors to produce, for example, in vivo biotinylated antibodies, scFv-Fc or complete IgG. Preferably, according to the present invention, antibodies in the scFv-Fc format are used because they are a functionally identical alternative to IgG in most tests, and, due to their faster and easier production, provide a robust format for screening a large number of antibody candidates and can be converted into complete IgG later.

In the process of generating antibodies by phage display, the antibodies against the target of interest can be selected by panning. Thus, in the panning procedure, according to the present invention, the KLK7 antigen is immobilized on a solid surface, such as array column, nitrocellulose, magnetic spheres, or, plastic surfaces with high protein binding capacity such as polystyrene tubes.

For the development of the antibodies, or fragments thereof, according to the present invention, for example, in microtiter wells (MTPs), phage from antibody libraries are incubated with the antigen bound to the surface, followed by rigorous washing to remove the excess of unbound antibody phage. Subsequently, the bound antibody phage is eluted and re-amplified by *E. coli* infection. The selection cycle is repeated by infecting *E. coli* colonies carrying phagemids, derived from the first panning round with a helperphage to produce new antibody phages, which can be used for further panning rounds, until significant enrichment of antigen-specific antibody phages is achieved.

The number of antigen-specific antibody phage clones shall increase after each panning round. In accordance with the present invention, 2 to 5 panning rounds are carried out to select antibody fragments which specifically bind. Preferably, 3 rounds of selection are carried out.

In further accordance with the present invention, after selection, the gene fragments encoding the antibody fragments can be subcloned into any other format, for example scFv-Fc or IgG according to any known method.

Alternatively, the nucleotide sequences of the selected phages can be used to create new libraries to be used in an affinity maturation process and selected again by the processes described above.

Thus, in a specific manner, the present invention relates to the antibodies generated and selected according to the methods described above, or fragments thereof, as described below.

Table 1: List of antibodies and amino acid sequences.

TABLE 1

| List of antibodies and amino acid sequences. | |
|---|---|
| Antibody | Amino acid sequence |
| LUP-14B2 | SEQ ID #2 |
| LUP-14C4 | SEQ ID #4 |
| LUP-14D6 | SEQ ID #6 |
| LUP-14E9 | SEQ ID #8 |
| LUP-14E12 | SEQ ID #10 |
| LUP-14F7 | SEQ ID #12 |
| LUP-14F10 | SEQ ID #14 |
| LUP-14G8 | SEQ ID #16 |
| LUP-14G10 | SEQ ID #18 |
| LUP37-A10 | SEQ ID #20 |
| LUP37-B10 | SEQ ID #22 |
| LUP37-C11 | SEQ ID #24 |
| LUP37-D11 | SEQ ID #26 |

Another aspect of the present invention relates to a nucleic acid encoding a polypeptide, wherein each amino acid residue of the polypeptide is encoded by one or more (at least one) codons. The term "amino acid" denotes the group α-amino acid which directly or in the form of a precursor can be encoded by a nucleic acid. Individual amino acids are encoded by nucleic acids consisting of three nucleotides, known as codons or triplet of bases. Each amino acid is encoded by at least one codon. The fact that the same amino acid is encoded by different codons is known as "degeneracy of the genetic code". The term "amino acid", as used in the present application, denotes the α-amino acids that naturally occur, comprising alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine.

The term "codon" denotes an oligonucleotide consisting of three nucleotides encoding a defined amino acid. Due to the degeneracy of the genetic code, most amino acids are encoded by more than one codon. These different codons that encode the same amino acid have different relative frequencies of use in different organisms. Therefore, a specific amino acid is encoded either by an exact codon or by a group of different codons. Likewise, the amino acid sequence of a polypeptide can be encoded by different nucleic acids. Therefore, a specific amino acid (residue) in a polypeptide can be encoded by a group of different codons, each of these codons having a frequency of use within a given cell or organism.

Thus, one skilled in the art knows that different species can demonstrate "preferential codon usage". As used herein, the term "preferred codon usage" or "preferred codons" is a term in the art related to protein translation codons that are used most frequently in cells of a certain species, thus favoring one among a few of possible representative codons encoding each amino acid. For example, the amino acid threonine (Thr) may be encoded by ACA, ACC, ACG, or ACT, but in mammalian cells, ACC is the most commonly used codon; in other species, for example insect cells, yeast, virus or bacteria, different Thr codons may be preferential.

As a large number of gene sequences from different organisms is currently available, it is possible to calculate the relative frequencies of codon usage in different organisms. Illustratively, codon usage tables are available in "Codon Usage Database"., at www(dot)kazusa(dot)or(dot) jp/codon/ (Nakamura et al., 2000. Nucl. Acids Res. V. 28, p. 292) and in EMBOSS (The European Molecular Biology Open Software Suite (Rice et al., 2000. Trends Gen. v. 16, pp. 276-277). The tool available at https://www(dot)idtdna (dot)com/CodonOpt also can be used.

It is evident that due to the degeneracy of the genetic code and the possibility of a variation in the nucleotide sequence without affecting the amino acid sequence of the encoded polypeptide. Accordingly, the present invention relates to any nucleic acid encoding all or any functional portion of the amino acid sequences shown in SEQ ID #2, 4, 6, 8, 10, 12, 14, 16, 18, 20, 22, 24 and 26.

Preferably, the present invention relates to the nucleotide sequences shown in SEQ ID #1, 3, 5, 7, 9, 11, 13, 15, 17, 19, 21, 23 and 25, or any sequence that has at least 80% of similarity with these sequences.

As the antibodies, or fragments thereof, of the present invention show an inhibitory action on KLK7, they can preferably be used for the prophylaxis or treatment of diseases or disorders caused by the over expression or increased activity of this enzyme. Examples of use of these compounds would be for the treatment of dermatological diseases, especially those related to desquamation. More specifically, the compounds of the present invention can be used, for example, for the prophylaxis and/or treatment of atopic dermatitis, psoriasis and Netherton syndrome.

Antibodies, or fragments thereof, according to the present invention, may also be used as the active ingredient of a pharmaceutical agent of the present invention. The route of administration of the pharmaceutical agent of the present invention is not particularly limited, and the agent can be administered orally or parenterally. Preferably, however, they are to be administered as a preparation in the form of a pharmaceutical composition containing the active ingredient and at least one pharmaceutically or pharmacologically acceptable additive.

Further, in accordance with the present invention, the antibodies, or fragments thereof, described herein, are incorporated into formulations suitable for topical use.

Examples of formulations suitable for topical administration include suspensions, emulsions, spray lotions, unguents, creams, gels, patches, films, ointments, and compositions incorporated into patches, all of which are known in the art of topical formulations and preparations. Gel, lotion, cream and ointment formulations are preferred in accordance with the present invention. Even more preferably, the formulation according to the present invention is in the form of hydrogels. Most preferably, the formulations according to the present invention are in the form of hydrogels based on poloxamers, such as poloxamer 407 and poloxamer 403.

Among the adjuvants and excipients that can be additionally used for the preparation of the compositions according to the present invention, the following can be highlighted:

permeation enhancers, such as dibutyl adipate, isopropyl myristate, dimethyl sufoxide, diethylene glycol monoethyl ether, propylene glycol dicaprylocaprate, isopropyl myristate, sodium lauryl sulfate, polyoxyethylene sorbitan monooleate and sorbitan monolaurate;

fatty alcohols having from about 4 to about 30 carbon atoms, such as stearyl alcohol, cetyl alcohol, cetostearyl alcohol, myristyl alcohol;

emollients such as dibutyl adipate, diisobutyl adipate, diisopropyl adipate, dimethicone, triglyceride esters of fatty acids such as caprylic/capric triglycerides, hydroxylated lanolin, isopropyl myristate, mineral oil, soy sterol, cetyl stearate and petrolatum, linolenic acid, linoleic acid and oleic acid;

emulsifiers such as steareth-2, steareth-21, glyceryl monostearate SE (a mixture of glyceryl stearate and PEG-100 stearate) and laureth-4, cetearyl, sorbitan, and ceteareth from mixtures of fatty acid esters resulting from the saponification of vegetable oil, selected among coconut oil, palm oil, olive oil, soybean oil, sunflower seed oil or animal oil;

humectants such as glycerin, propylene glycol, sorbitol, lactose, mannitol, pyrrolidone sodium carboxylic acid, panthenol, hyaluronic acid, chondroitin;

amphoteric surfactants such as saponins, lecithin and soy proteins; and moisturizers such as trehalose, maltose and sucrose;

as well as any combinations or mixtures thereof, in addition to other similar and equivalent compounds.

Other additives can be incorporated into the compositions of the present invention, such as ultraviolet absorbers or sunscreens, antioxidants, preservatives and others, for improved stability during use and storage. Non-limiting examples of suitable antioxidants and appropriate preservatives include, but are not limited to, butylated hydroxytoluene, butylated hydroxyanisole (BHA), sorbic acid, benzoic acid, benzyl alcohol, imidazolidinyl urea, diazolidinyl urea, methylparaben, propylparaben, potassium sorbate and mixtures or combinations thereof.

It should also be understood that the compositions of the present invention may include other components commonly used in conventional topical cosmetic formulations such as suspending agents, thickening agents, film formers, preservatives and fragrance oils. The thickening agents are preferably those which are compatible with the composition, such as bentones, xanthan gum, silica and ethyl cellulose. Dyes, fragrances and other cosmetic additives may also be present. The exemplified and specifically enumerated cosmetic components may be freely substituted with other conventional and well known components, to obtain a desired texture and lubricity of the compositions, provided that the substitutes do not adversely react with any component of the composition and do not interfere with the homogeneity of the composition.

The present invention is also described by the non-limiting examples below, which are merely illustrative. Several modifications and variations of the embodiments are evident to the one person skilled in the art, without moving away from the spirit and scope of the invention.

Numerous variations concerning the protection scope of the present application are allowed. Thus, it reinforces the fact that the present invention is not limited to the particular configurations/embodiments described above.

Examples

Obtaining Active Human Tissue Kallikrein 7 (KLK7)

The KLK7 used was obtained in the recombinant form from an insect/baculovirus cell system as previously described by Teixeira et al.

The enzyme produced by the methodology described above is expressed fused with a 6 histidine tag and an enterokinase cleavage site at the N-terminus of the enzyme. Therefore, after the purification on a Ni-NTA column (interacts with the 6-Histidine tag), the enzyme was incubated with enterokinase for 20 hours at 18° C., at a ratio of 1:100 (enterokinase: KLKs), in 50 mM Tris buffer (pH=8.0), for histidine tag removal and enzyme activation.

Activation was monitored by hydrolysis of the substrate Abz-KLFSQ-EDDnp. The separation between KLK7, with an approximate mass of 30 kDa, and enterokinase, which has a mass of 150 kDa, was carried out in FPLC (Fast Protein Liquid Chromatography) using gel filtration on a superdex column. Enzyme quantification was performed by spectrophotometry, using a wavelength of 280 nm and the KLK7 molar extinction coefficient.

Tests to Determine the KLKs Catalytic Activity

Initially the activity of KLK7 was monitored using substrate with fluorescence intramolecular suppression Abz-KLFSQ-EDDnp. This experiment was performed on a Hitachi F2500 spectrofluorimeter adjusted with 5 nm excitation and emission slits and wavelengths adjusted to $\lambda_{em}$=320 nm and $\lambda_{ex}$=420 nm, respectively. For this purpose, a quartz cuvette with an optical path of 10 mm and a final volume of 1 mL was used.

The enzyme and 100 mM Tris-HCl buffer solution (pH=7.5) were added to the cuvette, kept in a thermostated compartment at 37° C. for 5 minutes. After this time, the substrate with fluorescence intramolecular suppression was added and the velocity of the enzyme hydrolysis was determined by the increase in fluorescence as a function of time, and converted into nmol of hydrolyzed substrate per minute. The hydrolysis kinetic parameters ($K_m$ and $V_{max}$) were determined by Lineweaver-Burk graphs ($1/V \times 1/[S]$) according to equation 1 below:

$$\frac{1}{v} = \frac{K_m}{V_{máx}[S]} + \frac{1}{V_{máx}}$$

Antibodies Selection

5 µg of recombinant KLK7 were immobilized per well in high affinity 96-well plates overnight, 4° C.

The selection was made as described by Russo et al. (2018).

After the immobilization of recombinant KLK7, the plate was washed 3 times with PBST and incubated with blocking solution (MPBST) overnight, 4° C. After incubation it was washed 3 times with PBST.

$10^{12}$ phage particles from HAL9/10 library (approximately in excess of 80 times the phage particles when compared to the library size) were diluted in 50 µL of blocking solution for panning. This incubation was carried out for 1 hour at room temperature and it is necessary to remove nonspecific binders. The library, now pre-incubated, was added to the wells of the high-affinity plate previously incubated with recombinant KLK7. For the interaction between phages and KLK7, a 2-hour incubation at room temperature was performed.

Removal of non-specific binders was done by washing with PBST (10 times in the first round of selection, 20 times in the second, 30 times in the third and so on).

After washing, the phages, that strongly interacted with KLK7, were eluted with 150 µL of trypsin (10 µg/mL), for 30 minutes at 37° C.

50 mL of 2×YT medium were inoculated with overnight culture of E. coli TG1 and grown at 250 rpm, 37° C. till O.D.$_{600}$~0.5. 150 µl of TG1 were transferred to deepwell polypropylene plates, along with the eluted phage from the panning process. The plate was incubated for 30 minutes at 37° C. without agitation and then 30 minutes at 37° C. and 650 rpm.

1000 µL of 2×YT medium+150 µL 10×GA was then added and incubated for 1 hour, 37° C. and 650 rpm. The O.D. should reach ~0.5 (~5×10$^8$ cells/mL).

The bacteria are then infected with 50 µL of M13K07 helper phage (2×10$^{11}$ phage particles/mL) and incubated for 30 minutes, 37° C. without agitation, followed by a 30 minute incubation, 37° C., 650 rpm.

The plate is then centrifuged at 3220×g for 10 minutes. The supernatant is completely removed and 950 µL of 2×YT-AK is added to the pellet. It is incubated overnight, 30° C., 850 rpm for phage production.

In the other day, the plate is centrifuged at 3220×g. The supernatant contains the phages.

The panning (or bioselection) process was repeated three times. In the last bioselection, 10 µL of the eluted phages were used to determine the titer.

Titration of the Selected Phages

After the last panning, 10 µL of the eluted phages were used for the titer determination.

A culture of E. coli XL1-Blue MRF was grown in 2×YT-T overnight, 37° C., 250 rpm. In the next day, 500 µL of the culture was inoculated into 50 mL of 2×YT-T medium and kept at 37° C., 250 rpm until O.D.$_{600}$~0.5.

A serial dilution of the phages was done ($10^{-2}$-$10^{-12}$) in PBS. Each 10 µL of the dilution was then infected with 50 µL of bacteria and incubated for 30 minutes at 37° C. After growth, they were plated on 2×YT-GA agar plates and incubated overnight at 37° C.

In the other day, the colonies were counted and the calculated titer was 10$^7$.

Production of scFv Fragments

A 96-well polypropylene U-shaped plate was used for the production of selected antibody fragments.

150 µL of 2×YT-GA were added to each well and a clone from the last panning round was inoculated using a sterile pipet tip. The plate was incubated overnight for growth, at 37° C., 850 rpm.

In the other day a new 96-well polypropylene plate was prepared, this time with 180 µL of 2×YT-GA and 10 µL of the overnight clone growth. This plate was incubated for 2 hours, 37° C. and 850 rpm.

The plate was centrifuged at 3220×g for 10 minutes and the supernatant discarded by inversion. The pellet was then resuspended in 180 µL of 2×YT-A+50 µM of IPTG and the plate was incubated overnight for phages production, at 30° C., 800 rpm.

In the other day, the antibodies were screened by ELISA.

Antibody Fragments ELISA

For ELISA screening, two flat bottom ELISA plates are sensitized with 1 µg of KLK7, overnight, at 4° C.

The plate with the produced phages is centrifuged at 3220×g for 10 minutes and 40 µL of the supernatant is added to the KLK7 sensitized plates. 60 µL of MPBST 2% are added and the plate is incubated at room temperature for 1.5 hours.

Plates are washed with ultrapure water Milli-Q® nonionic polyoxyethelyne surfactant TweenTM 0.005% and primary antibody (mouse a-myc tag 9E10; 1:50, diluted in MPBST 2%) is added to each well. The plates are incubated for 1.5 hours, under gentle agitation, at room temperature and are then washed again with ultrapure water_Milli-Q®+ nonionic polyoxyethelyne surfactant_Tween™ 0.005%.

Secondary antibody (goat a-mouse IgG Fab specific HRP A0168; 1:700, diluted in MPBST 2%) is added to each well and the plate is incubated for 1.5 hours at room temperature, under gentle agitation. The plate is then washed and 100 μL of developer solution (TMB) are added to each well. The development is incubated for 35 minutes and 100 μL of $H_2SO_4$ are added to stop the reaction.

Plates are then read at 450 nm and 620 nm to find positive hits.

The antibodies that demonstrated interaction efficiency greater than 0.1 were subjected to DNA sequencing where it was found that nine different scFv sequences against KLK7 were selected (FIG. 1). They were: LUP-14B12, LUP-14C4, LUP-14D6, LUP-14E9, LUP-14E12, LUP-14F7, LUP-14F10, LUP-14G8 and LUP-14G10.

These antibody fragments (scFv) were selected in the pHAL30 expression vector and were recloned into the pCSE2.6-hIG1-Fc-Xp vector, for expression in HEK cells, in an IgG-like (scFv-Fc) antibody format. The antibody genes, now inserted into the pCSE2.6-hIG1-Fc-Xp vector, were transfected into HEK293-6E cells and, after their production, purified with protein A, as described by Beer et al. (Toxins, 2018).

Inhibitory Tests Against KLK7

After production and purification, the 9 antibodies selected from the HAL9/10 library had their $IC_{50}$ determined.

TABLE 2

| $IC_{50}$ of the antibodies selected against KLK7 from the naïve HAL9/10 library. | |
| --- | --- |
| Clone | $IC_{50}$ (nM) |
| LUP-14B2 | 275.0 |
| LUP-1 4C4 | 365.5 |
| LUP-1406 | 79.9 |
| LUP-14E9 | 420.0 |
| LUP-14E12 | 273.0 |
| LUP-14P7 | 151.5 |
| LUP-14F10 | 18.9 |
| LUP-1408 | 100.8 |
| LUP-14G10 | 2.3 |

$IC_{50}$ represents the concentration of drug or substance that is required to inhibit 50% of the activity of the compound of interest. The antibody was selected for having the lowest $IC_{50}$, since, with 2.3 nM, it is possible to obtain a 50% inhibition of the KLK7 activity. All other selected antibodies were specific against KLK7, but with different affinities, reflected in the high $IC_{50}$ values, therefore, we chose LUP-14G10 to undergo the affinity maturation process.

Affinity Maturation by Phage Display

Affinity maturation is a process that occurs naturally, when the immune system comes into contact with the same antigen more than once (EISEN, Cancer Immunol Res, 2014). This process is responsible for increasing the affinity of specific antibodies to their antigens, the result of a process of natural selection that alternates somatic hypermutation of Igs genes with selection and clonal expansion of B lymphocytes, which have acquired mutations capable of increasing affinity (TAS et al., Science, 2016).

Affinity maturation was performed according to the protocol developed by Thie et al. (Therapeutical antibodies, 2009) and Kügler et al. (Phage display: methods and protocols, 2018).

The first step was the amplification of the LUP-14G10 antibody gene by PCR. The PCR product was purified and digested with NcoI and Hind III enzymes, according to the manufacturers' instructions.

The digestion product was cloned into the vector pHAL30-VL, belonging to a HAL9/10 light chain library, designed for affinity maturation of antibodies selected from the naïve HAL9/10 library. The light chain library contains the variation of all light chains of all antibodies in the naïve library, but there is a space for insertion of the heavy chain gene of the antibody for which maturation is desired. Thus, the VH insert of the LUP-14G10 antibody was bound to the pHAL30-VL vector using T4 ligase, following the manufacturers' instructions.

The bound product was purified and, subsequently, transfected by electroporation into electrocompetent *E. coli* ER2738. The library was grown for 1 hour, at 37° C. and 600 rpm.

For the production of the LUP-14G10 antibody light chain library, 10 μL of the library was added to 990 μL of 2×YT. 10 μL were put aside for library titration (serial dilution from $10^{-2}$ till $10^{-6}$). The titration was performed as previously described.

The remaining 990 μL were plated on an agar plate (pizza plate) which was incubated overnight at 37° C. In the following day, 25 mL of 2×YT were added to the pizza plate and the colonies were detached from the agar with the aid of a Drigalsky loop. The library was then frozen with glycerol.

For the packaging of the library, 200 mL of 2×YT-GA were inoculated with 1 mL of the library. It was grown at 250 rpm, 37° C. until O.D.$_{600}$~0.5. Two 25 mL aliquots were then separated and infected with $2.5 \times 10^{11}$ M13K07 helper phage forming units.

The aliquots were incubated for 30 minutes at 37° C. without agitation and, later, under the same conditions, but under agitation (250 rpm). After incubation they were centrifuged at 3220×g for 20 minutes. The pellet was resuspended in 200 mL of 2×YT-AK and the phages were produced overnight at 30° C., 250 rpm.

After phage production the bacteria are centrifuged for 10 minutes, 10000×g. The supernatant is transferred to a new tube and ⅕ of the volume of the PEG solution is added for phage precipitation. For precipitation, this solution was incubated for one hour at 4° C. under gentle agitation.

After incubation it was centrifuged for 10 minutes at 10000×g; the supernatant was discarded and the pellet resuspended in 10 mL of phage dilution buffer. 1/5 of the PEG volume was added again and the solution was incubated at 4° C. under gentle agitation for 20 minutes.

Phages were centrifuged at 10000×g for 30 minutes; the supernatant was discarded and the pellet was resuspended in 1 mL of phage dilution buffer. The library was then stored in refrigerator.

Library titration was performed as previously explained.

Selection of Antibodies from the LUP-14G10 Antibody Light Chain Library

In possess of the light chain library created from the original antibody LUP-14G10, it was possible to select new antibodies, in the same way as described in the item "Antibodies Selection". The procedures were the same, with the exception that, instead of the naïve HAL9/10 library, the library created with the LUP-14G10 antibody heavy chain was used. After the selection rounds, the production of scFv fragments and subsequent ELISA were performed to identify positive hits. The antibodies were cloned into the expression vector for mammalian cells, produced in the scFv-Fc format and purified with protein A.

Figure 4:
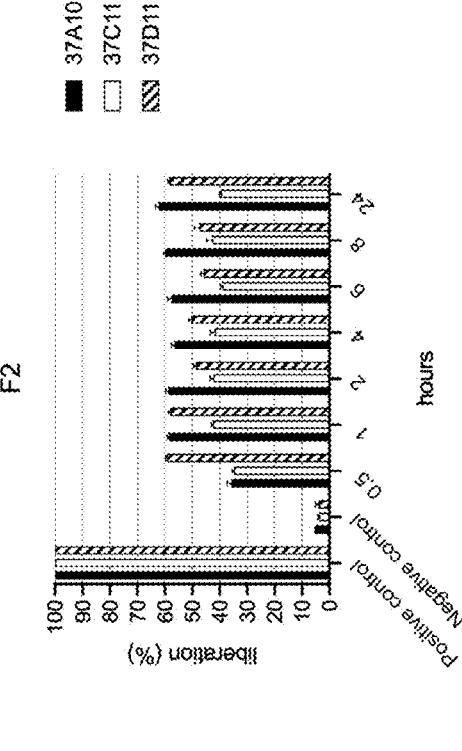
FIG. 4: In vitro antibody release profile after encapsulation in both poloxamer formulations. Detection was performed through indirect ELISA.
Figure 4:
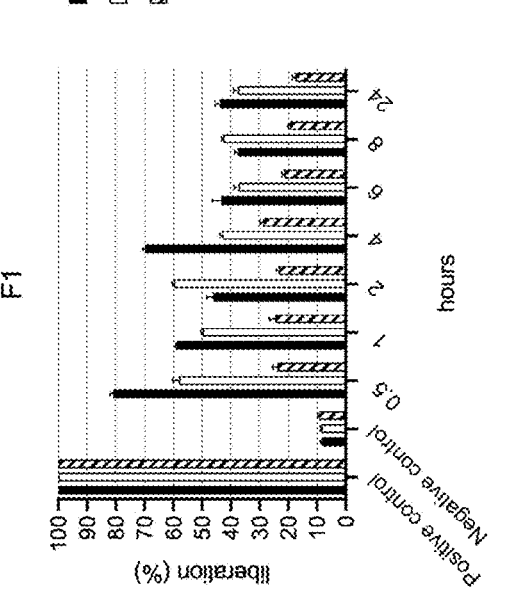

From the new library, 4 new antibodies against KLK7 were identified: LUP-37A10, LUP-37B10, LUP-37C11 and LUP-37D11 (FIG. 4).

The selected antibodies were characterized for $IC_{50}$. Table 3 contains these data.

TABLE 3

| IC$_{50}$ of antibodies produced from clone LUP-14G10 after the affinity maturation process. | |
| --- | --- |
| Clone | IC$_{50}$ (nM) |
| LUP-14G10 | 2.3 |
| LUP-37A10 | 0.81 |
| LUP-37B10 | 6.1 |
| LUP-37C11 | 0.52 |
| LUP-37D11 | 0.95 |

It can be seen that 3 antibodies were selected with the $IC_{50}$ lower than the $IC_{50}$ value of the original antibody. The selected antibodies exhibit $IC_{50}$'s below 1 nM, being lower than that of the original antibody by up to 4 times, which makes them ideal for use as inhibitors similar to endogenous inhibitors in skin pathologies.

Drug Delivery System Characterization

Formulations Composition

The drug delivery system was standardized in two formulations, as shown in the table below:

TABLE 1

| Formulations composition used to standardize the drug delivery system. | |
| --- | --- |
| Formulation | Composition |
| F1 | 30% PL407 |
| F2 | 2% PL403 + 28% PL407 |

Poloxamer 407 (Pluronic® F-127) and poloxamer 403 (Pluronic® F-123) were diluted in ultrapure water Milli-Q® in an ice bath due to the thermo-reversible characteristics of these copolymers.

The incorporation of antibodies to the formulations was also done in an ice bath, under agitation, for 1 hour, in the proportion of 1 μL of antibody to 1 mL of formulation. 1 μL of ultrapure water Milli-Q® was added in place of antibodies for control.

Physicochemical Characterization (DLS and Rheological Analysis)

For the DLS readings, the formulations were prepared as described above. Antibodies were added to the formulations 24 hours before analysis. The final concentration of antibody in the formulation was 1 μg/mL.

Readings were taken on the Zetasizer Nano ZS apparatus (Malvern Panalytical Ltd.). Disposable polystyrene cuvettes (10 mm, 4.5 mL) were used to determine the size of the particles. Measurements were taken at two temperatures: 25° C. and 32.5° C. and repeated 3 times. The results are described in table 5.

TABLE 2

| Hydrodynamic diameter (nm) and mean distribution (%) values for *micellae* formed only by PL407 or associated with PL403 before and after the addition of antibodies. | | | | |
| --- | --- | --- | --- | --- |
| | 25° C. | | 32.5° C. | |
| Formulation | Hydrodynamic diameter (nm) | Mean distribution (%) | Hydrodynamic diameter (nm) | Mean distribution (%) |
| F1 | 28.81 ± 0.9 | 80 | 22.99 ± 0.1 | 84 |
| F2 | 31.79 ± 0.3 | 87 | 23.97 ± 0.2 | 93 |
| F1 LUP-37A10 | 14.86 ± 0.3 | 41 | 11.59 ± 0.5 | 43 |
| F2 LUP-37A10 | 31.35 ± 1.1 | 94 | 21.15 ± 1.1 | 98 |
| F1 LUP-37C11 | 14.86 ± 1.3 | 41 | 11.59 ± 1.3 | 43 |
| F2LUP-37C11 | 32.02 ± 0.3 | 86 | 21.79 ± 0.3 | 95 |
| F1 LUP-37D11 | 30.22 ± 0.1 | 83 | 22.48 ± 0.1 | 84 |
| F2 LUP-37D11 | 26.14 ± 0.7 | 92 | 22.32 ± 0.6 | 94 |

For the rheological characterization, hydrogels, with the antibodies previously incorporated, were kept on ice, to remain in the liquid state when loaded in the rheometer. The rheometer used was the Kinexus rotational (Malvern Instruments Ltd.). The sample was analyzed using the cone-plate morphology (40 mm).

To determine the transition temperature (T sol-gel), the analyzes were performed with a temperature ramp, ranging from 10 to 50° C., with the space of 1 mm between plates, frequency of 1 Hz and shear stress of 2 Pa. A frequency sweep was also performed, ranging from 0.1 to 10 Hz (at 32.5° C.). The sample volume applied was always 1 mL and each analysis was performed 3 times.

All data, obtained through the rSpace Kinexus software, were used to determine the elastic modulus (G'), viscous modulus (G") and viscosity (ii). The collected data can be seen in table 6.

TABLE 6

| Rheological analysis of elastic (G') and viscous (G") moduli at transition temperature (T sol-gel), viscosity (η at 25 and 32.5° C.) and the transition temperature for F1 and F2 formulations. | | | | | | |
| --- | --- | --- | --- | --- | --- | --- |
| | | | | | η (mPa/s) | |
| Formulation | G' (mPa) | G" (mPa) | G'/G" | T sol-gel (° C.) | 10° C. | 32.5° C. |
| F1 | 9143598 | 38513330 | 0.24 | 18.30 | $5.85 \times 10^7$ | $3.49 \times 10^9$ |
| F1 LUP-37A10 | 99919760 | 22766430 | 4.39 | 17.00 | $7.025 \times 10^7$ | $3.31 \times 10^{12}$ |
| F1 LUP-37C11 | 3235000 | 801500 | 4.04 | 18.65 | $5.88 \times 10^4$ | $3.22 \times 10^9$ |
| F1 LUP-37D11 | 5126000 | 1830000 | 2.80 | 18.93 | $5.037 \times 10^4$ | $3.19 \times 10^9$ |
| F2 | 52247 | 14292670 | 0.00 | 18.68 | $5.169 \times 10^7$ | $3.30 \times 10^{12}$ |
| F2 LUP-37A10 | 70350800 | 61165330 | 1.15 | 18.65 | $5.498 \times 10^7$ | $3.277 \times 10^{12}$ |

TABLE 6-continued

Rheological analysis of elastic (G') and viscous (G") moduli at
transition temperature (T sol-gel), viscosity (η at 25 and 32.5° C.) and the
transition temperature for F1 and F2 formulations.

| | | | | | η (mPa/s) | |
|---|---|---|---|---|---|---|
| Formulation | G' (mPa) | G" (mPa) | G'/G" | T sol-gel (° C.) | 10° C. | 32.5° C. |
| F2 LUP-37C11 | 11650 | 142600 | 0.08 | 19.80 | $4.664 \times 10^4$ | $2.409 \times 10^9$ |
| F2 LUP-37D11 | 44660 | 344100 | 0.13 | 20.04 | $4.125 \times 10^4$ | $2.705 \times 10^9$ |

In Vitro Release Test

For the in vitro release test a glass tube was connected to the bottom of a 40 mL beaker. 1 mL of each formulation was added to the glass tube and, once gelled, the beaker was then filled with 40 mL of saline solution 0.9%. A magnetic agitator was placed inside the beaker and the system was maintained at 32.5° C. for 24 hours, under constant magnetic agitation (350 rpm). At different time intervals (30 minutes, 1, 2, 4, 6, 8 and 24 hours) 1 mL was collected and stored at −20° C. for inhibitory analysis against recombinant KLK7.

The antibodies were identified by indirect ELISA. Correlating the concentration of antibodies produced by phage display with the absorbance reading (450/630 nm), it is possible to obtain a graph, whose linear equation is used for quantification.

For quantification, high binding plates were incubated overnight at 4° C. with 5 ng/μL of recombinant KLK7. Primary antibodies (LUP-37A10, LUP-37C11 and LUP-37D11) were added in serial dilution (1 μg/mL-0.015 μg/mL) and incubated for 1.5 hours at room temperature. The plate was washed and the secondary antibody (goat anti-human IgG peroxidase labeled—KPL antibodies and conjugates) was added according to the manufacturer's instructions and incubated at room temperature for 45 minutes. After the development, the reading at 450 and 630 nm was performed in a Synergy HT fluorescence reader (Biotek Instruments).

Figure 3:
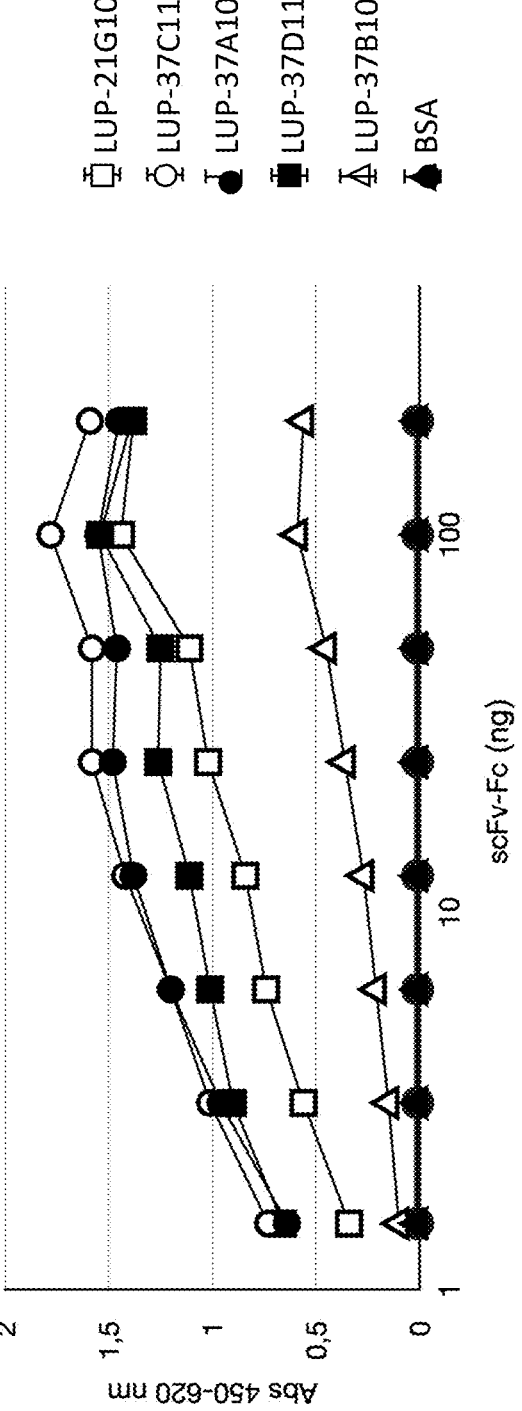
FIG. 3: Titration of clones generated from the LUP-14G10 clone affinity maturation process.

FIG. 3 contains the antibody release graphs for F1 and F2 formulations.

Inhibitory Activity Test of the Released Antibodies Against Recombinant KLK7

The inhibitory activity test was performed to verify whether the amount of antibody released from within the micellae, in the in vitro release test, would have inhibitory activity against recombinant KLK7.

Figure 5:
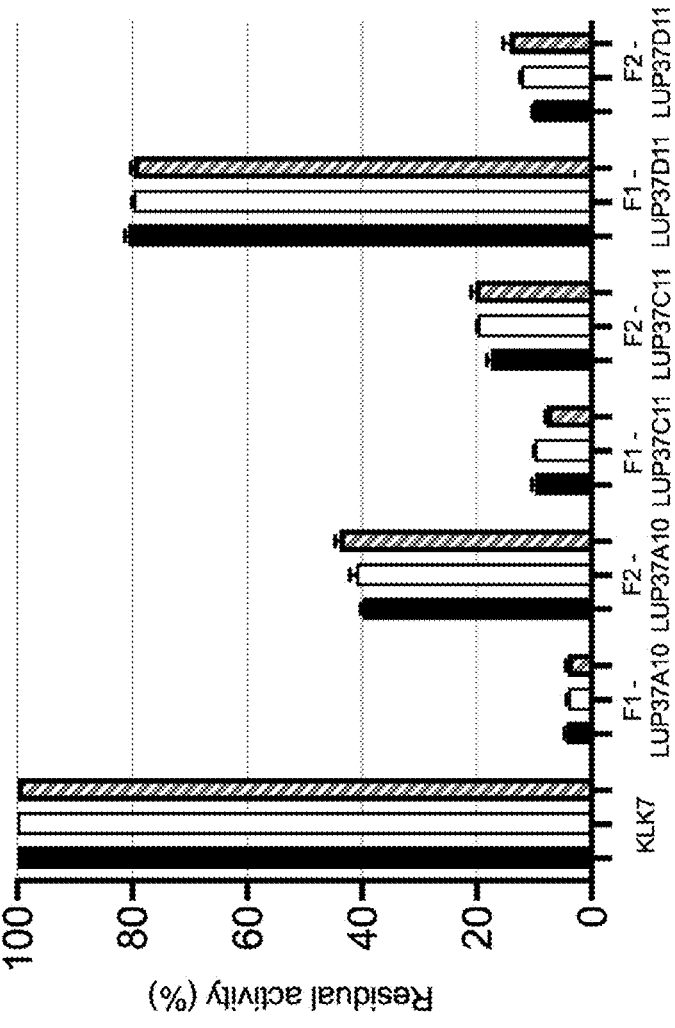
FIG. 5: Inhibitory profile of antibodies after the in vitro release test upon 6, 8 and 24 hours.

The test was performed using FRET substrate specific for KLK7, Abz-KLYSQ-EDDnp (1 mg/mL). Recombinant KLK7 (5 ng/μL) diluted in PBS (pH=7.4) was added to black polystyrene plates, ideal for fluorescence reading. Test buffer (50 mM Tris buffer, pH=7.5) was then added and incubated for 2 minutes at 37° C. The substrate was then added and 15-minute readings were taken at 37° C., under agitation. The positive control was done with KLK7 only. To assess antibody activity, an aliquot of 100 μL from the sampling times of 6, 8 and 24 hours were added before the addition of the substrate. FIG. 5 shows the results of the inhibitory test for the antibodies encapsulated in both formulations.

The invention claimed is:

1. An antibody, or a fragment thereof, wherein the antibody comprises the amino acids sequence of any one of SEQ ID NO: 18, 20, 22, 24 or 26.

2. The antibody, or a fragment thereof, according to claim 1, wherein the antibody consists of the amino acids sequence of any one of SEQ ID NO: #18, 20, 22, 24 or 26.

3. The antibody, or a fragment thereof, according to claim 1, wherein the antibody is an scFv, scFv-Fc or IgG antibody.

4. A nucleotide sequence encoding an antibody, or a fragment thereof, according to claim 1.

5. The nucleotide sequence, according to claim 4, wherein the nucleotide sequence comprises a nucleic acid sequence of any one of SEQ ID NO: #17, 19, 21, 23 and 25.

6. The nucleotide sequence, according to claim 4, wherein the nucleotide sequence consists of the nucleic acid sequence of any one of SEQ ID NO: #17, 19, 21, 23 and 25.

7. A composition comprising an antibody, or a fragment thereof, according to claim 1.

8. The composition, according to claim 7, formulated for topical use.

9. The composition, according to claim 7, in the form of a suspension, emulsion, spray lotion, unguent, cream, gel, plaster, film, ointment or incorporated into patches.

10. The composition, according to claim 7, in the form of a gel, lotion, cream or ointment.

11. The composition, according to claim 10, in the form of a hydrogel.

12. The composition, according to claim 9, wherein the gel is a poloxamer-based hydrogel.

13. The composition, according to claim 12, wherein the poloxamer is poloxamer 407 and/or poloxamer 403.

14. A method for treating or preventing KLK7-related diseases or disorders, comprising administering an antibody, or fragment thereof, according to claim 1, or a composition comprising an antibody according to claim 2, to a subject in need thereof.

15. A method according to claim 14, wherein the dermatological pathology is selected from atopic dermatitis, psoriasis and Netherton syndrome.

* * * * *

SEQUENCE LISTING

<160> NUMBER OF SEQ ID NOS: 26

<210> SEQ ID NO 1
<211> LENGTH: 804
<212> TYPE: DNA
<213> ORGANISM: Artificial sequence
<220> FEATURE:
<223> OTHER INFORMATION: antibody

<400> SEQUENCE: 1

```
ccatggccca ggtacagctg cagcagtcag gcccaggact ggtgcagcct tcggagaccc      60
tgtccctcac gtgcactgtc tctggtggct ccatgaatag ttactattgg agctggatcc     120
ggcagcccgc cgggaaggga ctggagtgga tcgggcgtgt ctatcccact gggggaaccg     180
actacaaccc ctccctcaag agtcgagtca taatgtcagt agacacggtt cggaaccact     240
tctccctgag attgaactct gtgaccgccg cggactcggc cgtgtattac tgtgcgagag     300
atcggggcta cagtaactac ggctggttcg acccctgggg ccagggaacc ctggtcaacg     360
tctcctcagg gagtgcatcc gccccaaagc ttgaagaagg tgaattttca gaagcacgcg     420
taaattttat gctgactcag ccccactctg tgtcggcgtc tccggggaag acggtaacca     480
tctcctgcac cggcagcagt ggcagcattg ccagcaactt tgtacagtgg taccagcagc     540
gcccgggcag tgcccccacc actgtgatct atgaagataa tcaaagaccc tctggggtcc     600
```

-continued

```
ctgatcggtt ctccggctcc atcgacagtt cgtccaactc tgcctccctc agcatctctg      660
gactgcagac tgacgacgag gctgactact actgtcagtc ttctgatagc agcaatcacg      720
tggtgttcgg cggagggacc aagctgaccg tcctaggtca gcccaaggct gcccctcgg       780 tcactctgtt cccaccgtcc tctg                                            804
```

```
<210> SEQ ID NO 2
<211> LENGTH: 498
<212> TYPE: PRT
<213> ORGANISM: Artificial sequence
<220> FEATURE:
<223> OTHER INFORMATION: antibody

<400> SEQUENCE: 2

Met Ala Gln Val Gln Leu Gln Gln Ser Gly Pro Gly Leu Val Gln Pro
1               5                   10                  15

Ser Glu Thr Leu Ser Leu Thr Cys Thr Val Ser Gly Gly Ser Met Asn
                20                  25                  30

Ser Tyr Tyr Trp Ser Trp Ile Arg Gln Pro Ala Gly Lys Gly Leu Glu
            35                  40                  45

Trp Ile Gly Arg Val Tyr Pro Thr Gly Gly Thr Asp Tyr Asn Pro Ser
        50                  55                  60

Leu Lys Ser Arg Val Ile Met Ser Val Asp Thr Val Arg Asn His Phe
65                  70                  75                  80

Ser Leu Arg Leu Asn Ser Val Thr Ala Ala Asp Ser Ala Val Tyr Tyr
                85                  90                  95

Cys Ala Arg Asp Arg Gly Tyr Ser Asn Tyr Gly Trp Phe Asp Pro Trp
            100                 105                 110

Gly Gln Gly Thr Leu Val Asn Val Ser Ser Gly Ser Ala Ser Ala Pro
        115                 120                 125

Lys Leu Glu Glu Gly Glu Phe Ser Glu Ala Arg Val Asn Phe Met Leu
    130                 135                 140

Thr Gln Pro His Ser Val Ser Ala Ser Pro Gly Lys Thr Val Thr Ile
145                 150                 155                 160

Ser Cys Thr Gly Ser Ser Gly Ser Ile Ala Ser Asn Phe Val Gln Trp
                165                 170                 175

Tyr Gln Gln Arg Pro Gly Ser Ala Pro Thr Thr Val Ile Tyr Glu Asp
            180                 185                 190

Asn Gln Arg Pro Ser Gly Val Pro Asp Arg Phe Ser Gly Ser Ile Asp
        195                 200                 205

Ser Ser Ser Asn Ser Ala Ser Leu Ser Ile Ser Gly Leu Gln Thr Asp
    210                 215                 220

Asp Glu Ala Asp Tyr Tyr Cys Gln Ser Ser Asp Ser Ser Asn His Val
225                 230                 235                 240

Val Phe Gly Gly Gly Thr Lys Leu Thr Val Leu Gly Gln Pro Lys Ala
                245                 250                 255

Ala Pro Ser Val Thr Leu Phe Pro Pro Ser Ser Ala Ala Ala Ser Asp
            260                 265                 270

Lys Thr His Thr Cys Pro Pro Cys Pro Ala Pro Glu Leu Leu Gly Gly
        275                 280                 285

Pro Ser Val Phe Leu Phe Pro Pro Lys Pro Lys Asp Thr Leu Met Ile
    290                 295                 300

Ser Arg Thr Pro Glu Val Thr Cys Val Val Val Asp Val Ser His Glu
305                 310                 315                 320
```

```
Asp Pro Glu Val Lys Phe Asn Trp Tyr Val Asp Gly Val Glu Val His
            325                 330                 335

Asn Ala Lys Thr Lys Pro Arg Glu Glu Gln Tyr Asn Ser Thr Tyr Arg
            340                 345                 350

Val Val Ser Val Leu Thr Val Leu His Gln Asp Trp Leu Asn Gly Lys
            355                 360                 365

Glu Tyr Lys Cys Lys Val Ser Asn Lys Ala Leu Pro Ala Pro Ile Glu
        370                 375                 380

Lys Thr Ile Ser Lys Ala Lys Gly Gln Pro Arg Glu Pro Gln Val Tyr
385                 390                 395                 400

Thr Leu Pro Pro Ser Arg Glu Glu Val Thr Lys Asn Gln Val Ser Leu
                405                 410                 415

Thr Cys Leu Val Lys Gly Phe Tyr Pro Ser Asp Ile Ala Val Glu Trp
            420                 425                 430

Glu Ser Asn Gly Gln Pro Glu Asn Asn Tyr Lys Thr Thr Pro Pro Val
            435                 440                 445

Leu Asp Ser Asp Gly Ser Phe Phe Leu Tyr Ser Lys Leu Thr Val Asp
        450                 455                 460

Lys Ser Arg Trp Gln Gln Gly Asn Val Phe Ser Cys Ser Val Met His
465                 470                 475                 480

Glu Ala Leu His Asn His Tyr Thr Gln Lys Ser Leu Ser Leu Ser Pro
                485                 490                 495

Gly Lys
```

<210> SEQ ID NO 3
<211> LENGTH: 801
<212> TYPE: DNA
<213> ORGANISM: Artificial sequence
<220> FEATURE:
<223> OTHER INFORMATION: antibody

<400> SEQUENCE: 3

```
ccatggccca ggttcagctg gtgcagtctg ggggaggcgt ggtccagcct gggaggtccc      60
tgagactctc ctgtgcagcc tctggattca tcttcagtga ttattctatg cattgggtcc     120
gccaggctcc aggcaagggg ctggagtggg tggcagttat gtcatatgat gcaaggagtc     180
aattctacgc agactccgtg aagggccgat tcaccatctc cagagacaat tccaagaaca     240
ctctatatct gcaaatgaac agcctgagag aggaagacac ggctgtgtat tactgtgcga     300
cagatgttgg caattccccg tttgactact ggggccaggg aaccctggtc accgtctcct     360
cagggagtgc atccgcccca aagcttgaag aaggtgaatt ccagaagca cgcgtacagg      420 ctgtgctgac tcagcccccc tcagtgtctg ggccctagg gcagagggtc accatctcct      480
gcactgggag cagctccaac atcggggcgc cttatgatgt acactggtac cagcagcttc     540
caggaacagc ccccaaactc ctcatatacg gtaataacaa tcggccctca ggggtccctg     600
accgattctc tggctccaag tctggcacct cagcctccct ggccatcagt gggctccggt     660
ccgaggatga ggctgattat tactgtgcag catgggatga cagcctgagt ggttcttggg     720
tgttcggcgg agggaccaag ctgaccgtcc taggtcagcc caaggctgcc ccctcggtca     780
ctctgttccc accgtcctct g                                               801
```

<210> SEQ ID NO 4
<211> LENGTH: 497
<212> TYPE: PRT
<213> ORGANISM: Artificial sequence
<220> FEATURE:

<223> OTHER INFORMATION: antibody

<400> SEQUENCE: 4

Met Ala Gln Val Gln Leu Val Gln Ser Gly Gly Val Val Gln Pro
1               5                   10                  15

Gly Arg Ser Leu Arg Leu Ser Cys Ala Ala Ser Gly Phe Ile Phe Ser
            20                  25                  30

Asp Tyr Ser Met His Trp Val Arg Gln Ala Pro Gly Lys Gly Leu Glu
        35                  40                  45

Trp Val Ala Val Met Ser Tyr Asp Ala Arg Ser Gln Phe Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Glu Glu Asp Thr Ala Val Tyr
                85                  90                  95

Tyr Cys Ala Thr Asp Val Gly Asn Ser Pro Phe Asp Tyr Trp Gly Gln
            100                 105                 110

Gly Thr Leu Val Thr Val Ser Ser Gly Ser Ala Ser Ala Pro Lys Leu
            115                 120                 125

Glu Glu Gly Glu Phe Ser Glu Ala Arg Val Gln Ala Val Leu Thr Gln
        130                 135                 140

Pro Pro Ser Val Ser Gly Ala Leu Gly Gln Arg Val Thr Ile Ser Cys
145                 150                 155                 160

Thr Gly Ser Ser Ser Asn Ile Gly Ala Pro Tyr Asp Val His Trp Tyr
                165                 170                 175

Gln Gln Leu Pro Gly Thr Ala Pro Lys Leu Leu Ile Tyr Gly Asn Asn
            180                 185                 190

Asn Arg Pro Ser Gly Val Pro Asp Arg Phe Ser Gly Ser Lys Ser Gly
            195                 200                 205

Thr Ser Ala Ser Leu Ala Ile Ser Gly Leu Arg Ser Glu Asp Glu Ala
    210                 215                 220

Asp Tyr Tyr Cys Ala Ala Trp Asp Asp Ser Leu Ser Gly Ser Trp Val
225                 230                 235                 240

Phe Gly Gly Gly Thr Lys Leu Thr Val Leu Gly Gln Pro Lys Ala Ala
                245                 250                 255

Pro Ser Val Thr Leu Phe Pro Pro Ser Ser Ala Ala Ala Ser Asp Lys
            260                 265                 270

Thr His Thr Cys Pro Pro Cys Pro Ala Pro Glu Leu Leu Gly Gly Pro
            275                 280                 285

Ser Val Phe Leu Phe Pro Pro Lys Pro Lys Asp Thr Leu Met Ile Ser
    290                 295                 300

Arg Thr Pro Glu Val Thr Cys Val Val Val Asp Val Ser His Glu Asp
305                 310                 315                 320

Pro Glu Val Lys Phe Asn Trp Tyr Val Asp Gly Val Glu Val His Asn
            325                 330                 335

Ala Lys Thr Lys Pro Arg Glu Glu Gln Tyr Asn Ser Thr Tyr Arg Val
            340                 345                 350

Val Ser Val Leu Thr Val Leu His Gln Asp Trp Leu Asn Gly Lys Glu
            355                 360                 365

Tyr Lys Cys Lys Val Ser Asn Lys Ala Leu Pro Ala Pro Ile Glu Lys
        370                 375                 380

Thr Ile Ser Lys Ala Lys Gly Gln Pro Arg Glu Pro Gln Val Tyr Thr
385                 390                 395                 400

```
Leu Pro Pro Ser Arg Glu Glu Val Thr Lys Asn Gln Val Ser Leu Thr
            405             410             415

Cys Leu Val Lys Gly Phe Tyr Pro Ser Asp Ile Ala Val Glu Trp Glu
            420             425             430

Ser Asn Gly Gln Pro Glu Asn Asn Tyr Lys Thr Thr Pro Pro Val Leu
            435             440             445

Asp Ser Asp Gly Ser Phe Phe Leu Tyr Ser Lys Leu Thr Val Asp Lys
        450             455             460

Ser Arg Trp Gln Gln Gly Asn Val Phe Ser Cys Ser Val Met His Glu
465             470             475             480

Ala Leu His Asn His Tyr Thr Gln Lys Ser Leu Ser Leu Ser Pro Gly
            485             490             495

Lys
```

```
<210> SEQ ID NO 5
<211> LENGTH: 819
<212> TYPE: DNA
<213> ORGANISM: Artificial sequence
<220> FEATURE:
<223> OTHER INFORMATION: antibody

<400> SEQUENCE: 5
ccatggccca ggtgcagctg caggagtccg ggggaggctt ggtaaagcct ggggggtccc     60
ttagactctc ctgtgcagcc tctggattca ctttcagtaa cgcctggatg agctgggtcc    120
gccaggctcc agggaagggg ctggagtggg ttggccgtat taaaagcaaa actgatggtg    180
ggacaacaga ctacgctgca cccgtgaaag gcagattcac catctcaaga gatgattcaa    240
aaaacacgct gtatctgcaa atgaacagcc tgaaaaccga ggacacagcc gtgtattact    300
gtaccacagg gttggtcctt tattgtggtg gtgactgcta ccgtttgac tactggggcc    360 agggaaccct ggtcaccgtc tcctcaggga gtgcatccgc cccaaagctt gaagaaggtg    420
aattttcaga agcacgcgta ctgcctgtgc tgactcagcc accctcagcg tctgggaccc    480
ccgggcagag ggtcaccatc tcttgttctg gaagcagctc caacatcgaa acaaatactt    540
tgagctggta ccaacaactc ccaggaaggg ccccccaaact cctcatgcat aatgataatg    600
agcggccccc aggggtccct gaccgattct ctggctccaa gtctggcacc tcagcctccc    660
tggccatcag tgggctccaa tctgaggatg aggctgatta ttactgtgca gcatgggatg    720
acagtttgaa tggtcaggtg ttcggcggag ggaccaaggt gaccgtctta ggtcagccca    780
aggctgcccc ctcggtcact ctgttcccgc cgtcctctg                           819
```

```
<210> SEQ ID NO 6
<211> LENGTH: 503
<212> TYPE: PRT
<213> ORGANISM: Artificial sequence
<220> FEATURE:
<223> OTHER INFORMATION: antibody

<400> SEQUENCE: 6

Met Ala Gln Val Gln Leu Gln Glu Ser Gly Gly Gly Leu Val Lys Pro
1               5               10              15

Gly Gly Ser Leu Arg Leu Ser Cys Ala Ala Ser Gly Phe Thr Phe Ser
            20              25              30

Asn Ala Trp Met Ser Trp Val Arg Gln Ala Pro Gly Lys Gly Leu Glu
        35              40              45

Trp Val Gly Arg Ile Lys Ser Lys Thr Asp Gly Gly Thr Thr Asp Tyr
    50              55              60
```

-continued

```
Ala Ala Pro Val Lys Gly Arg Phe Thr Ile Ser Arg Asp Asp Ser Lys
65              70              75              80

Asn Thr Leu Tyr Leu Gln Met Asn Ser Leu Lys Thr Glu Asp Thr Ala
            85              90              95

Val Tyr Tyr Cys Thr Thr Gly Leu Val Leu Tyr Cys Gly Gly Asp Cys
            100             105             110

Tyr Pro Phe Asp Tyr Trp Gly Gln Gly Thr Leu Val Thr Val Ser Ser
            115             120             125

Gly Ser Ala Ser Ala Pro Lys Leu Glu Glu Gly Glu Phe Ser Glu Ala
            130             135             140

Arg Val Leu Pro Val Leu Thr Gln Pro Pro Ser Ala Ser Gly Thr Pro
145             150             155             160

Gly Gln Arg Val Thr Ile Ser Cys Ser Gly Ser Ser Ser Asn Ile Glu
                165             170             175

Thr Asn Thr Leu Ser Trp Tyr Gln Gln Leu Pro Gly Arg Ala Pro Lys
            180             185             190

Leu Leu Met His Asn Asp Asn Glu Arg Pro Pro Gly Val Pro Asp Arg
            195             200             205

Phe Ser Gly Ser Lys Ser Gly Thr Ser Ala Ser Leu Ala Ile Ser Gly
            210             215             220

Leu Gln Ser Glu Asp Glu Ala Asp Tyr Tyr Cys Ala Ala Trp Asp Asp
225             230             235             240

Ser Leu Asn Gly Gln Val Phe Gly Gly Gly Thr Lys Val Thr Val Leu
                245             250             255

Gly Gln Pro Lys Ala Ala Pro Ser Val Thr Leu Phe Pro Pro Ser Ser
            260             265             270

Ala Ala Ala Ser Asp Lys Thr His Thr Cys Pro Pro Cys Pro Ala Pro
            275             280             285

Glu Leu Leu Gly Gly Pro Ser Val Phe Leu Phe Pro Pro Lys Pro Lys
            290             295             300

Asp Thr Leu Met Ile Ser Arg Thr Pro Glu Val Thr Cys Val Val Val
305             310             315             320

Asp Val Ser His Glu Asp Pro Glu Val Lys Phe Asn Trp Tyr Val Asp
                325             330             335

Gly Val Glu Val His Asn Ala Lys Thr Lys Pro Arg Glu Glu Gln Tyr
            340             345             350

Asn Ser Thr Tyr Arg Val Val Ser Val Leu Thr Val Leu His Gln Asp
            355             360             365

Trp Leu Asn Gly Lys Glu Tyr Lys Cys Lys Val Ser Asn Lys Ala Leu
            370             375             380

Pro Ala Pro Ile Glu Lys Thr Ile Ser Lys Ala Lys Gly Gln Pro Arg
385             390             395             400

Glu Pro Gln Val Tyr Thr Leu Pro Pro Ser Arg Glu Glu Val Thr Lys
                405             410             415

Asn Gln Val Ser Leu Thr Cys Leu Val Lys Gly Phe Tyr Pro Ser Asp
            420             425             430

Ile Ala Val Glu Trp Glu Ser Asn Gly Gln Pro Glu Asn Asn Tyr Lys
            435             440             445

Thr Thr Pro Pro Val Leu Asp Ser Asp Gly Ser Phe Phe Leu Tyr Ser
            450             455             460

Lys Leu Thr Val Asp Lys Ser Arg Trp Gln Gln Gly Asn Val Phe Ser
465             470             475             480
```

-continued

```
Cys Ser Val Met His Glu Ala Leu His Asn His Tyr Thr Gln Lys Ser
                485                 490                 495

Leu Ser Leu Ser Pro Gly Lys
            500

<210> SEQ ID NO 7
<211> LENGTH: 795
<212> TYPE: DNA
<213> ORGANISM: Artificial sequence
<220> FEATURE:
<223> OTHER INFORMATION: antibody

<400> SEQUENCE: 7
ccatggccca ggtccagctg gtgcagtctg gggctgaggt gaagaagcct gggggctacag      60 tgaaaatctc ctgcaaggtt tctggataca ccttcaccga ctactacatg cactgggtgc     120
aacaggcccc tggaaaaggg cttgagtgga tgggacttgt tgatcctgaa gatggtgaaa     180
caatatacgc agagaagttc cagggcagag tcaccataac cgcggacacg tctacagaca     240
cagcctacat ggagctgagc agcctgagat ctgaggacac ggccgtgtat tactgtgcaa     300
caggcaatgt acgtaggata gactactggg ccagggaac cctggtcacc gtctcctcag     360
ggagtgcatc cgccccaaag cttgaagaag gtgaattttc agaagcacgc gtaaatttta     420
tgctgactca gccccactct gtgtcggagt ctccggggaa gacggtaacc atctcctgca     480
ccggcagcag tggcagcatt gccgacaact atgtgcagtg gtaccagcag cgcccgggca     540
gtgcccccat caatgtgatc tatgaggata ccaaagacc ctctgggtc cctgatcggt     600 tctctggctc catcgacagc tcctccaact ctgcctccct caccatctct ggactgaaga     660
ctgaggacga ggctgactac tactgtcagt cttatgatag cagcaatcat gtggtattcg     720
gcggagggac caagctgacc gtcctaggtc agcccaaggc tgcccctcg gtcactctgt     780 tcccaccgtc ttctg                                                     795

<210> SEQ ID NO 8
<211> LENGTH: 495
<212> TYPE: PRT
<213> ORGANISM: Artificial sequence
<220> FEATURE:
<223> OTHER INFORMATION: antibody

<400> SEQUENCE: 8

Met Ala Gln Val Gln Leu Val Gln Ser Gly Ala Glu Val Lys Lys Pro
1               5                   10                  15

Gly Ala Thr Val Lys Ile Ser Cys Lys Val Ser Gly Tyr Thr Phe Thr
            20                  25                  30

Asp Tyr Tyr Met His Trp Val Gln Gln Ala Pro Gly Lys Gly Leu Glu
        35                  40                  45

Trp Met Gly Leu Val Asp Pro Glu Asp Gly Glu Thr Ile Tyr Ala Glu
    50                  55                  60

Lys Phe Gln Gly Arg Val Thr Ile Thr Ala Asp Thr Ser Thr Asp Thr
65                  70                  75                  80

Ala Tyr Met Glu Leu Ser Ser Leu Arg Ser Glu Asp Thr Ala Val Tyr
                85                  90                  95

Tyr Cys Ala Thr Gly Asn Val Arg Arg Ile Asp Tyr Trp Gly Gln Gly
            100                 105                 110

Thr Leu Val Thr Val Ser Ser Gly Ser Ala Ser Ala Pro Lys Leu Glu
        115                 120                 125

Glu Gly Glu Phe Ser Glu Ala Arg Val Asn Phe Met Leu Thr Gln Pro
```

-continued

<div style="text-align:center">130            135            140</div>

His Ser Val Ser Glu Ser Pro Gly Lys Thr Val Thr Ile Ser Cys Thr
145            150            155            160

Gly Ser Ser Gly Ser Ile Ala Asp Asn Tyr Val Gln Trp Tyr Gln Gln
                165            170            175

Arg Pro Gly Ser Ala Pro Ile Asn Val Ile Tyr Glu Asp Asn Gln Arg
            180            185            190

Pro Ser Gly Val Pro Asp Arg Phe Ser Gly Ser Ile Asp Ser Ser Ser
            195            200            205

Asn Ser Ala Ser Leu Thr Ile Ser Gly Leu Lys Thr Glu Asp Glu Ala
    210            215            220

Asp Tyr Tyr Cys Gln Ser Tyr Asp Ser Ser Asn His Val Val Phe Gly
225            230            235            240

Gly Gly Thr Lys Leu Thr Val Leu Gly Gln Pro Lys Ala Ala Pro Ser
            245            250            255

Val Thr Leu Phe Pro Pro Ser Ser Ala Ala Ala Ser Asp Lys Thr His
            260            265            270

Thr Cys Pro Pro Cys Pro Ala Pro Glu Leu Leu Gly Gly Pro Ser Val
            275            280            285

Phe Leu Phe Pro Pro Lys Pro Lys Asp Thr Leu Met Ile Ser Arg Thr
    290            295            300

Pro Glu Val Thr Cys Val Val Val Asp Val Ser His Glu Asp Pro Glu
305            310            315            320

Val Lys Phe Asn Trp Tyr Val Asp Gly Val Glu Val His Asn Ala Lys
            325            330            335

Thr Lys Pro Arg Glu Glu Gln Tyr Asn Ser Thr Tyr Arg Val Val Ser
            340            345            350

Val Leu Thr Val Leu His Gln Asp Trp Leu Asn Gly Lys Glu Tyr Lys
            355            360            365

Cys Lys Val Ser Asn Lys Ala Leu Pro Ala Pro Ile Glu Lys Thr Ile
    370            375            380

Ser Lys Ala Lys Gly Gln Pro Arg Glu Pro Gln Val Tyr Thr Leu Pro
385            390            395            400

Pro Ser Arg Glu Glu Val Thr Lys Asn Gln Val Ser Leu Thr Cys Leu
            405            410            415

Val Lys Gly Phe Tyr Pro Ser Asp Ile Ala Val Glu Trp Glu Ser Asn
            420            425            430

Gly Gln Pro Glu Asn Asn Tyr Lys Thr Thr Pro Pro Val Leu Asp Ser
            435            440            445

Asp Gly Ser Phe Phe Leu Tyr Ser Lys Leu Thr Val Asp Lys Ser Arg
    450            455            460

Trp Gln Gln Gly Asn Val Phe Ser Cys Ser Val Met His Glu Ala Leu
465            470            475            480

His Asn His Tyr Thr Gln Lys Ser Leu Ser Leu Ser Pro Gly Lys
            485            490            495

<210> SEQ ID NO 9
<211> LENGTH: 783
<212> TYPE: DNA
<213> ORGANISM: Artificial sequence
<220> FEATURE:
<223> OTHER INFORMATION: antibody

<400> SEQUENCE: 9
ccatggccca agtccagctg gtgcagtctg gggctgaggt gaagaggcct ggggcctcag      60

-continued

```
tgaaggtctc ctgcaaggtt tccggataca ccctcactga attatccatg cactgggtgc      120
gacaggctcc tggaaaaggg cttgagtgga tgggaggttt tgatcctgaa gatggtgaaa      180
caatctacgc acagaagttc cagggcagag tcaccatgac cgaggacaca tctacagaca      240
cagcctacat ggagctgagc agcctgagat ctgaggacac ggccgtgtat tactgtgcaa      300
cattgaggca gtggctagaa tttgactact ggggccaggg aaccctggtc accgtctcct      360
cagggagtgc atccgcccca aagcttgaag aaggtgaatt ttcagaagca cgcgtacagt      420
ctgtgttgac gcagccgccc tcagtgtccg tgtccccagg acagacagcc agcatcacct      480
gctctggaga tagattgggg gataaatatg cttcctggta tcagcagaag ccaggccagt      540
cccctgtgct ggtcatctat caagatacca gcggccctc agggatccct gagcgattct      600
ctggctccaa ctctgggaac acagccactc tgaccatcag cgggacccag gctatggatg      660
aggctgacta ttactgtcag gcgtgggaca gcagcactgc ggtattcggc ggcgggacca      720
agctgaccgt cctaggtcag cccaaggctg cccctcggt cactctgttc ccaccgtcct      780
ctg                                                                    783
```

```
<210> SEQ ID NO 10
<211> LENGTH: 491
<212> TYPE: PRT
<213> ORGANISM: Artificial sequence
<220> FEATURE:
<223> OTHER INFORMATION: antibody

<400> SEQUENCE: 10

Met Ala Gln Val Gln Leu Val Gln Ser Gly Ala Glu Val Lys Arg Pro
1               5                   10                  15

Gly Ala Ser Val Lys Val Ser Cys Lys Val Ser Gly Tyr Thr Leu Thr
            20                  25                  30

Glu Leu Ser Met His Trp Val Arg Gln Ala Pro Gly Lys Gly Leu Glu
        35                  40                  45

Trp Met Gly Gly Phe Asp Pro Glu Asp Gly Glu Thr Ile Tyr Ala Gln
    50                  55                  60

Lys Phe Gln Gly Arg Val Thr Met Thr Glu Asp Thr Ser Thr Asp Thr
65                  70                  75                  80

Ala Tyr Met Glu Leu Ser Ser Leu Arg Ser Glu Asp Thr Ala Val Tyr
                85                  90                  95

Tyr Cys Ala Thr Leu Arg Gln Trp Leu Glu Phe Asp Tyr Trp Gly Gln
            100                 105                 110

Gly Thr Leu Val Thr Val Ser Ser Gly Ser Ala Ser Ala Pro Lys Leu
            115                 120                 125

Glu Glu Gly Glu Phe Ser Glu Ala Arg Val Gln Ser Val Leu Thr Gln
        130                 135                 140

Pro Pro Ser Val Ser Val Ser Pro Gly Gln Thr Ala Ser Ile Thr Cys
145                 150                 155                 160

Ser Gly Asp Arg Leu Gly Asp Lys Tyr Ala Ser Trp Tyr Gln Gln Lys
                165                 170                 175

Pro Gly Gln Ser Pro Val Leu Val Ile Tyr Gln Asp Thr Lys Arg Pro
            180                 185                 190

Ser Gly Ile Pro Glu Arg Phe Ser Gly Ser Asn Ser Gly Asn Thr Ala
            195                 200                 205

Thr Leu Thr Ile Ser Gly Thr Gln Ala Met Asp Glu Ala Asp Tyr Tyr
        210                 215                 220
```

-continued

```
Cys Gln Ala Trp Asp Ser Ser Thr Ala Val Phe Gly Gly Gly Thr Lys
225             230             235             240

Leu Thr Val Leu Gly Gln Pro Lys Ala Ala Pro Ser Val Thr Leu Phe
            245             250             255

Pro Pro Ser Ser Ala Ala Ala Ser Asp Lys Thr His Thr Cys Pro Pro
            260             265             270

Cys Pro Ala Pro Glu Leu Leu Gly Gly Pro Ser Val Phe Leu Phe Pro
            275             280             285

Pro Lys Pro Lys Asp Thr Leu Met Ile Ser Arg Thr Pro Glu Val Thr
        290             295             300

Cys Val Val Val Asp Val Ser His Glu Asp Pro Glu Val Lys Phe Asn
305             310             315             320

Trp Tyr Val Asp Gly Val Glu Val His Asn Ala Lys Thr Lys Pro Arg
                325             330             335

Glu Glu Gln Tyr Asn Ser Thr Tyr Arg Val Val Ser Val Leu Thr Val
            340             345             350

Leu His Gln Asp Trp Leu Asn Gly Lys Glu Tyr Lys Cys Lys Val Ser
        355             360             365

Asn Lys Ala Leu Pro Ala Pro Ile Glu Lys Thr Ile Ser Lys Ala Lys
    370             375             380

Gly Gln Pro Arg Glu Pro Gln Val Tyr Thr Leu Pro Pro Ser Arg Glu
385             390             395             400

Glu Val Thr Lys Asn Gln Val Ser Leu Thr Cys Leu Val Lys Gly Phe
                405             410             415

Tyr Pro Ser Asp Ile Ala Val Glu Trp Glu Ser Asn Gly Gln Pro Glu
            420             425             430

Asn Asn Tyr Lys Thr Thr Pro Pro Val Leu Asp Ser Asp Gly Ser Phe
            435             440             445

Phe Leu Tyr Ser Lys Leu Thr Val Asp Lys Ser Arg Trp Gln Gln Gly
    450             455             460

Asn Val Phe Ser Cys Ser Val Met His Glu Ala Leu His Asn His Tyr
465             470             475             480

Thr Gln Lys Ser Leu Ser Leu Ser Pro Gly Lys
            485             490
```

<210> SEQ ID NO 11
<211> LENGTH: 792
<212> TYPE: DNA
<213> ORGANISM: Artificial sequence
<220> FEATURE:
<223> OTHER INFORMATION: antibody

<400> SEQUENCE: 11

```
ccatggccca gctgcagcta cagcagtccg gcccaggact ggtgaagcct tcggggaccc      60
tgtccctcac ctgcgctgtc tctggtggct ccatcagcag tagtaactgg tggagttggg     120
tccgccagcc cccagggaag gggctggagt ggattgggga aatctatcat agtgggagca     180
ccaactacaa cccgtccctc aagagtcgag tcaccatatc agtagacaag tccaagaacc     240
agttctccct gaagctgagc tctgtgaccg ccgcggacac ggccgtgtat tactgtgcga     300
caggtacggc cagcttaatc ggtatggacg tctggggcca aggaccacg gtcaccgtct      360 cctcagggag tgcatccgcc ccaaagcttg aagaaggtga attttcagaa gcacgcgtat     420
cctatgtgct gactcagcca ccctcggtgt cagtggcccc aggacagacg gccaggattc     480
cctgtggggg aaataacatt ggagataaaa atgtgcagtg gtaccagcag aagccagacc     540
```

-continued

```
aggcccctgt gctggtcgtc tatgatgata gcgaccggcc ctcaggcatc cctgagcgat        600
tctctggctc caactctggg aacaaggccg ccctgaccat cagcggggtc gaggtcgggg        660
atgaggccga ctattattgt caggtgtggg ataggagttc tgatgtcgtg gtcttcggcg        720
gagggaccaa gctgaccgtc ctaggtcagc ccaaggctgc cccctcggtc actctgttcc        780
caccctcctc tg                                                           792
```

```
<210> SEQ ID NO 12
<211> LENGTH: 494
<212> TYPE: PRT
<213> ORGANISM: Artificial sequence
<220> FEATURE:
<223> OTHER INFORMATION: antibody

<400> SEQUENCE: 12

Met Ala Gln Leu Gln Leu Gln Gln Ser Gly Pro Gly Leu Val Lys Pro
1               5                   10                  15

Ser Gly Thr Leu Ser Leu Thr Cys Ala Val Ser Gly Gly Ser Ile Ser
            20                  25                  30

Ser Ser Asn Trp Trp Ser Trp Val Arg Gln Pro Pro Gly Lys Gly Leu
        35                  40                  45

Glu Trp Ile Gly Glu Ile Tyr His Ser Gly Ser Thr Asn Tyr Asn Pro
    50                  55                  60

Ser Leu Lys Ser Arg Val Thr Ile Ser Val Asp Lys Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Thr Gly Thr Ala Ser Leu Ile Gly Met Asp Val Trp Gly
            100                 105                 110

Gln Gly Thr Thr Val Thr Val Ser Ser Gly Ser Ala Ser Ala Pro Lys
            115                 120                 125

Leu Glu Glu Gly Glu Phe Ser Glu Ala Arg Val Ser Tyr Val Leu Thr
            130                 135                 140

Gln Pro Pro Ser Val Ser Val Ala Pro Gly Gln Thr Ala Arg Ile Pro
145                 150                 155                 160

Cys Gly Gly Asn Asn Ile Gly Asp Lys Asn Val Gln Trp Tyr Gln Gln
                165                 170                 175

Lys Pro Asp Gln Ala Pro Val Leu Val Val Tyr Asp Asp Ser Asp Arg
            180                 185                 190

Pro Ser Gly Ile Pro Glu Arg Phe Ser Gly Ser Asn Ser Gly Asn Lys
            195                 200                 205

Ala Ala Leu Thr Ile Ser Gly Val Glu Val Gly Asp Glu Ala Asp Tyr
        210                 215                 220

Tyr Cys Gln Val Trp Asp Arg Ser Ser Asp Val Val Val Phe Gly Gly
225                 230                 235                 240

Gly Thr Lys Leu Thr Val Leu Gly Gln Pro Lys Ala Ala Pro Ser Val
                245                 250                 255

Thr Leu Phe Pro Pro Ser Ser Ala Ala Ala Ser Asp Lys Thr His Thr
            260                 265                 270

Cys Pro Pro Cys Pro Ala Pro Glu Leu Leu Gly Gly Pro Ser Val Phe
            275                 280                 285

Leu Phe Pro Pro Lys Pro Lys Asp Thr Leu Met Ile Ser Arg Thr Pro
        290                 295                 300

Glu Val Thr Cys Val Val Val Asp Val Ser His Glu Asp Pro Glu Val
305                 310                 315                 320
```

```
Lys Phe Asn Trp Tyr Val Asp Gly Val Glu Val His Asn Ala Lys Thr
            325                 330                 335

Lys Pro Arg Glu Glu Gln Tyr Asn Ser Thr Tyr Arg Val Val Ser Val
            340                 345                 350

Leu Thr Val Leu His Gln Asp Trp Leu Asn Gly Lys Glu Tyr Lys Cys
            355                 360                 365

Lys Val Ser Asn Lys Ala Leu Pro Ala Pro Ile Glu Lys Thr Ile Ser
        370                 375                 380

Lys Ala Lys Gly Gln Pro Arg Glu Pro Gln Val Tyr Thr Leu Pro Pro
385                 390                 395                 400

Ser Arg Glu Glu Val Thr Lys Asn Gln Val Ser Leu Thr Cys Leu Val
            405                 410                 415

Lys Gly Phe Tyr Pro Ser Asp Ile Ala Val Glu Trp Glu Ser Asn Gly
            420                 425                 430

Gln Pro Glu Asn Asn Tyr Lys Thr Thr Pro Pro Val Leu Asp Ser Asp
            435                 440                 445

Gly Ser Phe Phe Leu Tyr Ser Lys Leu Thr Val Asp Lys Ser Arg Trp
        450                 455                 460

Gln Gln Gly Asn Val Phe Ser Cys Ser Val Met His Glu Ala Leu His
465                 470                 475                 480

Asn His Tyr Thr Gln Lys Ser Leu Ser Leu Ser Pro Gly Lys
            485                 490
```

```
<210> SEQ ID NO 13
<211> LENGTH: 798
<212> TYPE: DNA
<213> ORGANISM: Artificial sequence
<220> FEATURE:
<223> OTHER INFORMATION: antibody

<400> SEQUENCE: 13
ccatggccga ggtgcagctg gtggagtctg gggctgaggt gaagaagcct ggggcctcag      60
tgaaggtctc ctgcaaggtt tccggataca ccctcactga attatccatg cactgggtgc     120
gacagactcc tggaaaaggg cttgagtgga tgggaggttt tgatcctgaa gatggtgaaa     180
caatctacgc acagaagttc agggcagag tcaccatgac cgaggacaca tctacagaca     240
cagcctacat ggagctgagc agcctgagat ctgaggacac ggccgtgtat tactgtgcaa     300
cccaaggata tagtggctac gattactact ttgactactg gggccaggga accctggtca     360
ccgtctcctc agggagtgca tccgcccaa agcttgaaga aggtgaattt tcagaagcac      420
gcgtatcttc tgagctgact caggacccta ttgtgtctgt ggccttggga cagacagtca     480
ggatcgcttg ccaaggagac agcctcgaa cctcttatgc aagctggtac cagcagaagc      540
caggacaggc ccctgtactt gtcatgtacg gtaaaaacaa tcggccctca gggatccccg     600
accgattctc tggctcctac tcagggatct cagcttcctt gaccatcact ggggctcagg     660
cggaagatga ggctgactat tactgttact cccgggagac cactggatac cattatgtct     720
tcggaactgg gaccaaggtc accgtcctag gtcagcccaa ggccaacccc actgtcactc     780
tgttcccacc ctcctctg                                                    798

<210> SEQ ID NO 14
<211> LENGTH: 496
<212> TYPE: PRT
<213> ORGANISM: Artificial sequence
<220> FEATURE:
<223> OTHER INFORMATION: antibody
```

-continued

<400> SEQUENCE: 14

Met Ala Glu Val Gln Leu Val Glu Ser Gly Ala Glu Val Lys Lys Pro
1               5                   10                  15

Gly Ala Ser Val Lys Val Ser Cys Lys Val Ser Gly Tyr Thr Leu Thr
                20                  25                  30

Glu Leu Ser Met His Trp Val Arg Gln Thr Pro Gly Lys Gly Leu Glu
            35                  40                  45

Trp Met Gly Gly Phe Asp Pro Glu Asp Gly Glu Thr Ile Tyr Ala Gln
        50                  55                  60

Lys Phe Gln Gly Arg Val Thr Met Thr Glu Asp Thr Ser Thr Asp Thr
65                  70                  75                  80

Ala Tyr Met Glu Leu Ser Ser Leu Arg Ser Glu Asp Thr Ala Val Tyr
                85                  90                  95

Tyr Cys Ala Thr Gln Gly Tyr Ser Gly Tyr Asp Tyr Tyr Phe Asp Tyr
            100                 105                 110

Trp Gly Gln Gly Thr Leu Val Thr Val Ser Ser Gly Ser Ala Ser Ala
        115                 120                 125

Pro Lys Leu Glu Glu Gly Glu Phe Ser Glu Ala Arg Val Ser Ser Glu
    130                 135                 140

Leu Thr Gln Asp Pro Ile Val Ser Val Ala Leu Gly Gln Thr Val Arg
145                 150                 155                 160

Ile Ala Cys Gln Gly Asp Ser Leu Arg Thr Ser Tyr Ala Ser Trp Tyr
                165                 170                 175

Gln Gln Lys Pro Gly Gln Ala Pro Val Leu Val Met Tyr Gly Lys Asn
            180                 185                 190

Asn Arg Pro Ser Gly Ile Pro Asp Arg Phe Ser Gly Ser Tyr Ser Gly
        195                 200                 205

Ile Ser Ala Ser Leu Thr Ile Thr Gly Ala Gln Ala Glu Asp Glu Ala
    210                 215                 220

Asp Tyr Tyr Cys Tyr Ser Arg Glu Thr Thr Gly Tyr His Tyr Val Phe
225                 230                 235                 240

Gly Thr Gly Thr Lys Val Thr Val Leu Gly Gln Pro Lys Ala Asn Pro
                245                 250                 255

Thr Val Thr Leu Phe Pro Pro Ser Ser Ala Ala Ala Ser Asp Lys Thr
            260                 265                 270

His Thr Cys Pro Pro Cys Pro Ala Pro Glu Leu Leu Gly Gly Pro Ser
        275                 280                 285

Val Phe Leu Phe Pro Pro Lys Pro Lys Asp Thr Leu Met Ile Ser Arg
    290                 295                 300

Thr Pro Glu Val Thr Cys Val Val Val Asp Val Ser His Glu Asp Pro
305                 310                 315                 320

Glu Val Lys Phe Asn Trp Tyr Val Asp Gly Val Glu Val His Asn Ala
                325                 330                 335

Lys Thr Lys Pro Arg Glu Glu Gln Tyr Asn Ser Thr Tyr Arg Val Val
            340                 345                 350

Ser Val Leu Thr Val Leu His Gln Asp Trp Leu Asn Gly Lys Glu Tyr
        355                 360                 365

Lys Cys Lys Val Ser Asn Lys Ala Leu Pro Ala Pro Ile Glu Lys Thr
    370                 375                 380

Ile Ser Lys Ala Lys Gly Gln Pro Arg Glu Pro Gln Val Tyr Thr Leu
385                 390                 395                 400

Pro Pro Ser Arg Glu Glu Val Thr Lys Asn Gln Val Ser Leu Thr Cys

-continued

```
                   405                410                415

Leu Val Lys Gly Phe Tyr Pro Ser Asp Ile Ala Val Glu Trp Glu Ser
            420                425                430

Asn Gly Gln Pro Glu Asn Asn Tyr Lys Thr Thr Pro Pro Val Leu Asp
        435                440                445

Ser Asp Gly Ser Phe Phe Leu Tyr Ser Lys Leu Thr Val Asp Lys Ser
    450                455                460

Arg Trp Gln Gln Gly Asn Val Phe Ser Cys Ser Val Met His Glu Ala
465                470                475                480

Leu His Asn His Tyr Thr Gln Lys Ser Leu Ser Leu Ser Pro Gly Lys
            485                490                495
```

```
<210> SEQ ID NO 15
<211> LENGTH: 805
<212> TYPE: DNA
<213> ORGANISM: Artificial sequence
<220> FEATURE:
<223> OTHER INFORMATION: antibody

<400> SEQUENCE: 15
ccatggccca agtccagctg gtacagtctg gagcagaggt gaaaaagccc ggggagtctc      60
tgaggatctc ctgtaagggt tctgaataca gctttaccac ctcctggatc aactgggtgc     120
gccagatgcc cgggaaaggc ctggagtgga tggggaccat tgatcctagt gactcttata     180
ccgactacag cccgtccttc cgaggccacg tcaccatctc agttgacaag tccatcagta     240
ctgcctacct gcagtggagc agcctgaagg cctcagacac cgccgtctat tactgtgcga     300
ctccgtatag cacttctccc gggtccggtt cgactcctg gggccaggga accctggtca      360
ccgtctcctc agggagtgca tccgccccaa agcttgaaga aggtgaattt tcagaagcac     420
gcgtaaattt tatgctgact cagccccact ctgtgtcggg gtctccgggg aagacggtta     480
ccatctcctg taccgccaac ggtggcagcc ttgccaacaa ctttgtgcag tggtaccagc     540
agcgcccggg cagtgccccc acccctgtta tctatgagga tagtcaaaga ccctctgggg     600
tccctgatcg gttctctggc ttcatcgaca gctcctccaa ctctgcctcc ctcaccatct     660
ctggactgaa gactgaggac gaggctgatt actactgtca gtcttatgat aacaaagatt     720
gggtgttcgg cggagggacc aggctgaccg ttcctgggtc agcccaaggc tgccccctcg     780
gtcactctgt tcccgccctc ctctg                                         805

<210> SEQ ID NO 16
<211> LENGTH: 498
<212> TYPE: PRT
<213> ORGANISM: Artificial sequence
<220> FEATURE:
<223> OTHER INFORMATION: antibody

<400> SEQUENCE: 16

Met Ala Gln Val Gln Leu Val Gln Ser Gly Ala Glu Val Lys Lys Pro
1               5                   10                  15

Gly Glu Ser Leu Arg Ile Ser Cys Lys Gly Ser Glu Tyr Ser Phe Thr
            20                  25                  30

Thr Ser Trp Ile Asn Trp Val Arg Gln Met Pro Gly Lys Gly Leu Glu
        35                  40                  45

Trp Met Gly Thr Ile Asp Pro Ser Asp Ser Tyr Thr Asp Tyr Ser Pro
    50                  55                  60

Ser Phe Arg Gly His Val Thr Ile Ser Val Asp Lys Ser Ile Ser Thr
65                  70                  75                  80
```

-continued

```
Ala Tyr Leu Gln Trp Ser Ser Leu Lys Ala Ser Asp Thr Ala Val Tyr
                85                  90                  95

Tyr Cys Ala Thr Pro Tyr Ser Thr Ser Pro Gly Ser Gly Phe Asp Ser
            100                 105                 110

Trp Gly Gln Gly Thr Leu Val Thr Val Ser Ser Gly Ser Ala Ser Ala
            115                 120                 125

Pro Lys Leu Glu Glu Gly Glu Phe Ser Glu Ala Arg Val Asn Phe Met
    130                 135                 140

Leu Thr Gln Pro His Ser Val Ser Gly Ser Pro Gly Lys Thr Val Thr
145                 150                 155                 160

Ile Ser Cys Thr Ala Asn Gly Gly Ser Leu Ala Asn Asn Phe Val Gln
                165                 170                 175

Trp Tyr Gln Gln Arg Pro Gly Ser Ala Pro Thr Pro Val Ile Tyr Glu
            180                 185                 190

Asp Ser Gln Arg Pro Ser Gly Val Pro Asp Arg Phe Ser Gly Phe Ile
            195                 200                 205

Asp Ser Ser Ser Asn Ser Ala Ser Leu Thr Ile Ser Gly Leu Lys Thr
            210                 215                 220

Glu Asp Glu Ala Asp Tyr Tyr Cys Gln Ser Tyr Asp Asn Lys Asp Trp
225                 230                 235                 240

Val Phe Gly Gly Gly Thr Arg Leu Thr Val Leu Gly Gln Pro Lys Ala
                245                 250                 255

Ala Pro Ser Val Thr Leu Phe Pro Pro Ser Ser Ala Ala Ala Ser Asp
            260                 265                 270

Lys Thr His Thr Cys Pro Pro Cys Pro Ala Pro Glu Leu Leu Gly Gly
            275                 280                 285

Pro Ser Val Phe Leu Phe Pro Pro Lys Pro Lys Asp Thr Leu Met Ile
    290                 295                 300

Ser Arg Thr Pro Glu Val Thr Cys Val Val Val Asp Val Ser His Glu
305                 310                 315                 320

Asp Pro Glu Val Lys Phe Asn Trp Tyr Val Asp Gly Val Glu Val His
                325                 330                 335

Asn Ala Lys Thr Lys Pro Arg Glu Glu Gln Tyr Asn Ser Thr Tyr Arg
            340                 345                 350

Val Val Ser Val Leu Thr Val Leu His Gln Asp Trp Leu Asn Gly Lys
            355                 360                 365

Glu Tyr Lys Cys Lys Val Ser Asn Lys Ala Leu Pro Ala Pro Ile Glu
    370                 375                 380

Lys Thr Ile Ser Lys Ala Lys Gly Gln Pro Arg Glu Pro Gln Val Tyr
385                 390                 395                 400

Thr Leu Pro Pro Ser Arg Glu Glu Val Thr Lys Asn Gln Val Ser Leu
                405                 410                 415

Thr Cys Leu Val Lys Gly Phe Tyr Pro Ser Asp Ile Ala Val Glu Trp
            420                 425                 430

Glu Ser Asn Gly Gln Pro Glu Asn Asn Tyr Lys Thr Thr Pro Pro Val
            435                 440                 445

Leu Asp Ser Asp Gly Ser Phe Phe Leu Tyr Ser Lys Leu Thr Val Asp
    450                 455                 460

Lys Ser Arg Trp Gln Gln Gly Asn Val Phe Ser Cys Ser Val Met His
465                 470                 475                 480

Glu Ala Leu His Asn His Tyr Thr Gln Lys Ser Leu Ser Leu Ser Pro
                485                 490                 495
```

-continued

Gly Lys

<210> SEQ ID NO 17
<211> LENGTH: 811
<212> TYPE: DNA
<213> ORGANISM: Artificial sequence
<220> FEATURE:
<223> OTHER INFORMATION: antibody

<400> SEQUENCE: 17
ccatggccca ggtccagctg gtgcagtctg gggctgaggt gaagaagcct ggggcctcag      60
tgaaggtctc ctgcaaggtt tccggataca ccctcactga attatccatg cactgggtgc     120
gccagactcc tggaaaaggg cttgagtgga tgggaggttt tgatcctgaa gatggtgaaa     180
caatctacgc acagaagttc agggcagag tcaccatgac cgaggacaca tctacagaca     240
cagcctacat ggagctgagc agcctgaggt ctgaggacac ggccgtgtat tactgtgcaa     300
cccaaggata tagtggctac gattactact ttgactactg gggccaggga accctggtca     360
ccgtctcctc agggagtgca tccgccccaa agcttgaaga aggtgaattt tcagaagcac     420
gcgtacagtc tgtgttgacg cagccgccct cagcgtctgg accccccggg cagagggtca     480
ccatctcttg ttctggaagc agctccaaca tcggaagtaa tgctgtaaac tggtaccagc     540
agctcccagg aacggccccc aaactcctca tctatagtaa taatcaccgg ccctcagggg     600
tccctgaccg attctctggc tccaagtctg gcacctcagc ctccctggcc atcagtggac     660
tccagtctga ggatgaggct gattattact gtgcagcatg ggatgacggc ctgaatggtt     720
gggtgttcgg cggagggacc aagctgaccg tcctaggtca gcccaaggct gccccctcgg     780
tcactctgtt cccaccgtcc tctgcggccg c                                    811

<210> SEQ ID NO 18
<211> LENGTH: 498
<212> TYPE: PRT
<213> ORGANISM: Artificial sequence
<220> FEATURE:
<223> OTHER INFORMATION: antibody

<400> SEQUENCE: 18

Met Ala Gln Val Gln Leu Val Gln Ser Gly Ala Glu Val Lys Lys Pro
1               5                   10                  15

Gly Ala Ser Val Lys Val Ser Cys Lys Val Ser Gly Tyr Thr Leu Thr
            20                  25                  30

Glu Leu Ser Met His Trp Val Arg Gln Thr Pro Gly Lys Gly Leu Glu
        35                  40                  45

Trp Met Gly Gly Phe Asp Pro Glu Asp Gly Glu Thr Ile Tyr Ala Gln
    50                  55                  60

Lys Phe Gln Gly Arg Val Thr Met Thr Glu Asp Thr Ser Thr Asp Thr
65                  70                  75                  80

Ala Tyr Met Glu Leu Ser Ser Leu Arg Ser Glu Asp Thr Ala Val Tyr
                85                  90                  95

Tyr Cys Ala Thr Gln Gly Tyr Ser Gly Tyr Asp Tyr Tyr Phe Asp Tyr
            100                 105                 110

Trp Gly Gln Gly Thr Leu Val Thr Val Ser Ser Gly Ser Ala Ser Ala
        115                 120                 125

Pro Lys Leu Glu Glu Gly Glu Phe Ser Glu Ala Arg Val Gln Ser Val
    130                 135                 140

Leu Thr Gln Pro Pro Ser Ala Ser Gly Thr Pro Gly Gln Arg Val Thr
145                 150                 155                 160

-continued

```
Ile Ser Cys Ser Gly Ser Ser Ser Asn Ile Gly Ser Asn Ala Val Asn
                165                 170                 175

Trp Tyr Gln Gln Leu Pro Gly Thr Ala Pro Lys Leu Leu Ile Tyr Ser
                180                 185                 190

Asn Asn His Arg Pro Ser Gly Val Pro Asp Arg Phe Ser Gly Ser Lys
                195                 200                 205

Ser Gly Thr Ser Ala Ser Leu Ala Ile Ser Gly Leu Gln Ser Glu Asp
        210                 215                 220

Glu Ala Asp Tyr Tyr Cys Ala Ala Trp Asp Asp Gly Leu Asn Gly Trp
225                 230                 235                 240

Val Phe Gly Gly Gly Thr Lys Leu Thr Val Leu Gly Gln Pro Lys Ala
                245                 250                 255

Ala Pro Ser Val Thr Leu Phe Pro Pro Ser Ser Ala Ala Ala Ser Asp
                260                 265                 270

Lys Thr His Thr Cys Pro Pro Cys Pro Ala Pro Glu Leu Leu Gly Gly
        275                 280                 285

Pro Ser Val Phe Leu Phe Pro Pro Lys Pro Lys Asp Thr Leu Met Ile
    290                 295                 300

Ser Arg Thr Pro Glu Val Thr Cys Val Val Val Asp Val Ser His Glu
305                 310                 315                 320

Asp Pro Glu Val Lys Phe Asn Trp Tyr Val Asp Gly Val Glu Val His
                325                 330                 335

Asn Ala Lys Thr Lys Pro Arg Glu Glu Gln Tyr Asn Ser Thr Tyr Arg
                340                 345                 350

Val Val Ser Val Leu Thr Val Leu His Gln Asp Trp Leu Asn Gly Lys
        355                 360                 365

Glu Tyr Lys Cys Lys Val Ser Asn Lys Ala Leu Pro Ala Pro Ile Glu
    370                 375                 380

Lys Thr Ile Ser Lys Ala Lys Gly Gln Pro Arg Glu Pro Gln Val Tyr
385                 390                 395                 400

Thr Leu Pro Pro Ser Arg Glu Glu Val Thr Lys Asn Gln Val Ser Leu
                405                 410                 415

Thr Cys Leu Val Lys Gly Phe Tyr Pro Ser Asp Ile Ala Val Glu Trp
                420                 425                 430

Glu Ser Asn Gly Gln Pro Glu Asn Asn Tyr Lys Thr Thr Pro Pro Val
        435                 440                 445

Leu Asp Ser Asp Gly Ser Phe Phe Leu Tyr Ser Lys Leu Thr Val Asp
    450                 455                 460

Lys Ser Arg Trp Gln Gln Gly Asn Val Phe Ser Cys Ser Val Met His
465                 470                 475                 480

Glu Ala Leu His Asn His Tyr Thr Gln Lys Ser Leu Ser Leu Ser Pro
                485                 490                 495

Gly Lys
```

```
<210> SEQ ID NO 19
<211> LENGTH: 814
<212> TYPE: DNA
<213> ORGANISM: Artificial sequence
<220> FEATURE:
<223> OTHER INFORMATION: antibody

<400> SEQUENCE: 19
ccatggccca ggtccagctg gtgcagtctg gggctgaggt gaagaagcct ggggcctcag      60
tgaaggtctc ctgcaaggtt tccggataca ccctcactga attatccatg cactgggtgc     120
```

-continued

```
gccagactcc  tggaaaaggg  cttgagtgga  tgggaggttt  tgatcctgaa  gatggtgaaa        180
caatctacgc  acagaagttc  cagggcagag  tcaccatgac  cgaggacaca  tctacagaca        240
cagcctacat  ggagctgagc  agcctgaggt  ctgaggacac  ggccgtgtat  tactgtgcaa        300
cccaaggata  tagtggctac  gattactact  ttgactactg  gggccaggga  accctggtca        360
ccgtctcctc  agggagtgca  tccgccccaa  agcttgaaga  aggtgaattt  tcagaagcac        420
gcgtacaggc  tgtggtgact  caggagccat  cgttgtcagt  gtccctggga  gggacagtca        480
cactcagttg  tggattgagc  tctggctcag  tctcttctac  tcattatccc  agttggtacc        540
agcagacccc  aggccaggcc  ccacgtacac  tcatctacaa  cacaaacatt  cgctcttctg        600
gggtccctga  ccgattctct  ggctccaagt  ctggcacctc  agcctccctg  gccatcagtg        660
ggctccggtc  cgaggatgag  gctgattatt  actgtgcagc  atgggatgac  agcctgagtg        720
gttgggtgtt  cggcggaggg  accaagctga  ccgtcctagg  tcagcccaag  gctgcccct         780 cggtcactct  gttcccaccc  tcctctgcgg  ccgc                                      814
```

```
<210> SEQ ID NO 20
<211> LENGTH: 499
<212> TYPE: PRT
<213> ORGANISM: Artificial sequence
<220> FEATURE:
<223> OTHER INFORMATION: antibody

<400> SEQUENCE: 20

Met Ala Gln Val Gln Leu Val Gln Ser Gly Ala Glu Val Lys Lys Pro
1               5                   10                  15

Gly Ala Ser Val Lys Val Ser Cys Lys Val Ser Gly Tyr Thr Leu Thr
                20                  25                  30

Glu Leu Ser Met His Trp Val Arg Gln Thr Pro Gly Lys Gly Leu Glu
            35                  40                  45

Trp Met Gly Gly Phe Asp Pro Glu Asp Gly Glu Thr Ile Tyr Ala Gln
        50                  55                  60

Lys Phe Gln Gly Arg Val Thr Met Thr Glu Asp Thr Ser Thr Asp Thr
65                  70                  75                  80

Ala Tyr Met Glu Leu Ser Ser Leu Arg Ser Glu Asp Thr Ala Val Tyr
                85                  90                  95

Tyr Cys Ala Thr Gln Gly Tyr Ser Gly Tyr Asp Tyr Tyr Phe Asp Tyr
            100                 105                 110

Trp Gly Gln Gly Thr Leu Val Thr Val Ser Ser Gly Ser Ala Ser Ala
        115                 120                 125

Pro Lys Leu Glu Glu Gly Glu Phe Ser Glu Ala Arg Val Gln Ala Val
        130                 135                 140

Val Thr Gln Glu Pro Ser Leu Ser Val Ser Pro Gly Gly Thr Val Thr
145                 150                 155                 160

Leu Ser Cys Gly Leu Ser Ser Gly Ser Val Ser Thr His Tyr Pro
            165                 170                 175

Ser Trp Tyr Gln Gln Thr Pro Gly Gln Ala Pro Arg Thr Leu Ile Tyr
            180                 185                 190

Asn Thr Asn Ile Arg Ser Ser Gly Val Pro Asp Arg Phe Ser Gly Ser
        195                 200                 205

Lys Ser Gly Thr Ser Ala Ser Leu Ala Ile Ser Gly Leu Arg Ser Glu
        210                 215                 220

Asp Glu Ala Asp Tyr Tyr Cys Ala Ala Trp Asp Asp Ser Leu Ser Gly
225                 230                 235                 240
```

```
Trp Val Phe Gly Gly Gly Thr Lys Leu Thr Val Leu Gly Gln Pro Lys
            245                 250                 255

Ala Ala Pro Ser Val Thr Leu Phe Pro Pro Ser Ser Ala Ala Ala Ser
            260                 265                 270

Asp Lys Thr His Thr Cys Pro Pro Cys Pro Ala Pro Glu Leu Leu Gly
            275                 280                 285

Gly Pro Ser Val Phe Leu Phe Pro Pro Lys Pro Lys Asp Thr Leu Met
        290                 295                 300

Ile Ser Arg Thr Pro Glu Val Thr Cys Val Val Val Asp Val Ser His
305                 310                 315                 320

Glu Asp Pro Glu Val Lys Phe Asn Trp Tyr Val Asp Gly Val Glu Val
            325                 330                 335

His Asn Ala Lys Thr Lys Pro Arg Glu Glu Gln Tyr Asn Ser Thr Tyr
            340                 345                 350

Arg Val Val Ser Val Leu Thr Val Leu His Gln Asp Trp Leu Asn Gly
            355                 360                 365

Lys Glu Tyr Lys Cys Lys Val Ser Asn Lys Ala Leu Pro Ala Pro Ile
        370                 375                 380

Glu Lys Thr Ile Ser Lys Ala Lys Gly Gln Pro Arg Glu Pro Gln Val
385                 390                 395                 400

Tyr Thr Leu Pro Pro Ser Arg Glu Glu Val Thr Lys Asn Gln Val Ser
            405                 410                 415

Leu Thr Cys Leu Val Lys Gly Phe Tyr Pro Ser Asp Ile Ala Val Glu
            420                 425                 430

Trp Glu Ser Asn Gly Gln Pro Glu Asn Asn Tyr Lys Thr Thr Pro Pro
            435                 440                 445

Val Leu Asp Ser Asp Gly Ser Phe Phe Leu Tyr Ser Lys Leu Thr Val
        450                 455                 460

Asp Lys Ser Arg Trp Gln Gln Gly Asn Val Phe Ser Cys Ser Val Met
465                 470                 475                 480

His Glu Ala Leu His Asn His Tyr Thr Gln Lys Ser Leu Ser Leu Ser
            485                 490                 495

Pro Gly Lys
```

```
<210> SEQ ID NO 21
<211> LENGTH: 811
<212> TYPE: DNA
<213> ORGANISM: Artificial sequence
<220> FEATURE:
<223> OTHER INFORMATION: antibody

<400> SEQUENCE: 21
ccatggccca ggtccagctg gtgcagtctg gggctgaggt gaagaagcct ggggcctcag      60
tgaaggtctc ctgcaaggtt tccggataca ccctcactga attatccatg cactgggtgc     120
gccagactcc tggaaaaggg cttgagtgga tgggaggttt tgatcctgaa gatggtgaaa     180
caatctacgc acagaagttc agggcagag tcaccatgac cgaggacaca tctacagaca     240
cagcctacat ggagctgagc agcctgaggt ctgaggacac ggccgtgtat tactgtgcaa     300
cccaaggata tagtggctac gattactact ttgactactg gggccaggga accctggtca     360
ccgtctcctc agggagtgca tccgccccaa agcttgaaga aggtgaattt tcagaagcac     420
gcgtacaggc tgtgctgact cagccaccct cagcgtctgg acccccgggg cagagggtca     480
ccatctcttg ttctgggagc aactccaacg tcgggaggta tactgtaaac tggtaccaac     540
```

-continued

```
aactcccagg aacggccccc aaactcctca tcaatactaa tgatcggcgg ccctcagggg      600
tccctgaccg attctctggc tccaagtctg gcacctcagc ctccctggcc atcagtggcc      660
tccagtctga ggatgaggct gcttattact gtgcagcctg ggatgacagc cggaatggtt      720
gggcgttcgg cggagggacc aagctgaccg tcctccgtca gcccaaggct gccccctcgg      780
tcactctgtt cccgccctcc tctgcggccg c                                    811
```

```
<210> SEQ ID NO 22
<211> LENGTH: 498
<212> TYPE: PRT
<213> ORGANISM: Artificial sequence
<220> FEATURE:
<223> OTHER INFORMATION: antibody

<400> SEQUENCE: 22

Met Ala Gln Val Gln Leu Val Gln Ser Gly Ala Glu Val Lys Lys Pro
1               5                   10                  15

Gly Ala Ser Val Lys Val Ser Cys Lys Val Ser Gly Tyr Thr Leu Thr
            20                  25                  30

Glu Leu Ser Met His Trp Val Arg Gln Thr Pro Gly Lys Gly Leu Glu
        35                  40                  45

Trp Met Gly Gly Phe Asp Pro Glu Asp Gly Glu Thr Ile Tyr Ala Gln
    50                  55                  60

Lys Phe Gln Gly Arg Val Thr Met Thr Glu Asp Thr Ser Thr Asp Thr
65                  70                  75                  80

Ala Tyr Met Glu Leu Ser Ser Leu Arg Ser Glu Asp Thr Ala Val Tyr
                85                  90                  95

Tyr Cys Ala Thr Gln Gly Tyr Ser Gly Tyr Asp Tyr Tyr Phe Asp Tyr
            100                 105                 110

Trp Gly Gln Gly Thr Leu Val Thr Val Ser Ser Gly Ser Ala Ser Ala
        115                 120                 125

Pro Lys Leu Glu Glu Gly Glu Phe Ser Glu Ala Arg Val Gln Ala Val
        130                 135                 140

Leu Thr Gln Pro Pro Ser Ala Ser Gly Thr Pro Gly Gln Arg Val Thr
145                 150                 155                 160

Ile Ser Cys Ser Gly Ser Asn Ser Asn Val Gly Arg Tyr Thr Val Asn
                165                 170                 175

Trp Tyr Gln Gln Leu Pro Gly Thr Ala Pro Lys Leu Leu Ile Asn Thr
            180                 185                 190

Asn Asp Arg Arg Pro Ser Gly Val Pro Asp Arg Phe Ser Gly Ser Lys
        195                 200                 205

Ser Gly Thr Ser Ala Ser Leu Ala Ile Ser Gly Leu Gln Ser Glu Asp
        210                 215                 220

Glu Ala Ala Tyr Tyr Cys Ala Ala Trp Asp Asp Ser Arg Asn Gly Trp
225                 230                 235                 240

Ala Phe Gly Gly Gly Thr Lys Leu Thr Val Leu Arg Gln Pro Lys Ala
                245                 250                 255

Ala Pro Ser Val Thr Leu Phe Pro Pro Ser Ser Ala Ala Ala Ser Asp
            260                 265                 270

Lys Thr His Thr Cys Pro Pro Cys Pro Ala Pro Glu Leu Leu Gly Gly
        275                 280                 285

Pro Ser Val Phe Leu Phe Pro Pro Lys Pro Lys Asp Thr Leu Met Ile
        290                 295                 300

Ser Arg Thr Pro Glu Val Thr Cys Val Val Val Asp Val Ser His Glu
305                 310                 315                 320
```

```
Asp Pro Glu Val Lys Phe Asn Trp Tyr Val Asp Gly Val Glu Val His
            325                 330                 335

Asn Ala Lys Thr Lys Pro Arg Glu Glu Gln Tyr Asn Ser Thr Tyr Arg
            340                 345                 350

Val Val Ser Val Leu Thr Val Leu His Gln Asp Trp Leu Asn Gly Lys
            355                 360                 365

Glu Tyr Lys Cys Lys Val Ser Asn Lys Ala Leu Pro Ala Pro Ile Glu
    370                 375                 380

Lys Thr Ile Ser Lys Ala Lys Gly Gln Pro Arg Glu Pro Gln Val Tyr
385                 390                 395                 400

Thr Leu Pro Pro Ser Arg Glu Glu Val Thr Lys Asn Gln Val Ser Leu
            405                 410                 415

Thr Cys Leu Val Lys Gly Phe Tyr Pro Ser Asp Ile Ala Val Glu Trp
            420                 425                 430

Glu Ser Asn Gly Gln Pro Glu Asn Asn Tyr Lys Thr Thr Pro Pro Val
            435                 440                 445

Leu Asp Ser Asp Gly Ser Phe Phe Leu Tyr Ser Lys Leu Thr Val Asp
    450                 455                 460

Lys Ser Arg Trp Gln Gln Gly Asn Val Phe Ser Cys Ser Val Met His
465                 470                 475                 480

Glu Ala Leu His Asn His Tyr Thr Gln Lys Ser Leu Ser Leu Ser Pro
            485                 490                 495

Gly Lys

<210> SEQ ID NO 23
<211> LENGTH: 805
<212> TYPE: DNA
<213> ORGANISM: Artificial sequence
<220> FEATURE:
<223> OTHER INFORMATION: antibody

<400> SEQUENCE: 23
ccatggccca ggtccagctg gtgcagtctg gggctgaggt gaagaagcct gggggcctcag      60 tgaaggtctc ctgcaaggtt tccggataca ccctcactga attatccatg cactgggtgc     120
gccagactcc tggaaaaggg cttgagtgga tgggaggttt tgatcctgaa gatggtgaaa     180
caatctacgc acagaagttc cagggcagag tcaccatgac cgaggacaca tctacagaca     240
cagcctacat ggagctgagc agcctgaggt ctgaggacac ggccgtgtat tactgtgcaa     300
cccaaggata tagtggctac gattactact ttgactactg gggccaggga accctggtca     360
ccgtctcctc agggagtgca tccgccccaa agcttgaaga aggtgaattt tcagaagcac     420
gcgtatcttc tgagctgact caggaccctg ctgtgtctgt ggccttggga cagacagtca     480
ggatcacatg ccaaggagac agcctcagaa actattatgc aagctggtac cagcagaagc     540
caggacaggc ccccgtagtt gtcatctatg gtaaaaacaa ccggcccctca gggatcccag     600 accgattctc tggctccagc tcaggaaaca cagcttcctt gaccatcact ggggctcaag     660
cggaagatga ggctgactat tactgtaact cccgggacag cagtggtaac catgtggtat     720
tcggcggagg gaccaagctg accgtcctag gtcagtccaa ggctgcccccc tcggtcactc     780 tgttcccacc ctcctctgcg gccgc                                         805

<210> SEQ ID NO 24
<211> LENGTH: 496
<212> TYPE: PRT
<213> ORGANISM: Artificial sequence
```

<220> FEATURE:
<223> OTHER INFORMATION: antibody

<400> SEQUENCE: 24

```
Met Ala Gln Val Gln Leu Val Gln Ser Gly Ala Glu Val Lys Lys Pro
1               5                   10                  15

Gly Ala Ser Val Lys Val Ser Cys Lys Val Ser Gly Tyr Thr Leu Thr
                20                  25                  30

Glu Leu Ser Met His Trp Val Arg Gln Thr Pro Gly Lys Gly Leu Glu
            35                  40                  45

Trp Met Gly Gly Phe Asp Pro Glu Asp Gly Glu Thr Ile Tyr Ala Gln
        50                  55                  60

Lys Phe Gln Gly Arg Val Thr Met Thr Glu Asp Thr Ser Thr Asp Thr
65                  70                  75                  80

Ala Tyr Met Glu Leu Ser Ser Leu Arg Ser Glu Asp Thr Ala Val Tyr
                85                  90                  95

Tyr Cys Ala Thr Gln Gly Tyr Ser Gly Tyr Asp Tyr Tyr Phe Asp Tyr
            100                 105                 110

Trp Gly Gln Gly Thr Leu Val Thr Val Ser Ser Gly Ser Ala Ser Ala
        115                 120                 125

Pro Lys Leu Glu Glu Gly Glu Phe Ser Glu Ala Arg Val Ser Ser Glu
        130                 135                 140

Leu Thr Gln Asp Pro Ala Val Ser Val Ala Leu Gly Gln Thr Val Arg
145                 150                 155                 160

Ile Thr Cys Gln Gly Asp Ser Leu Arg Asn Tyr Tyr Ala Ser Trp Tyr
                165                 170                 175

Gln Gln Lys Pro Gly Gln Ala Pro Val Val Val Ile Tyr Gly Lys Asn
            180                 185                 190

Asn Arg Pro Ser Gly Ile Pro Asp Arg Phe Ser Gly Ser Ser Ser Gly
            195                 200                 205

Asn Thr Ala Ser Leu Thr Ile Thr Gly Ala Gln Ala Glu Asp Glu Ala
        210                 215                 220

Asp Tyr Tyr Cys Asn Ser Arg Asp Ser Ser Gly Asn His Val Val Phe
225                 230                 235                 240

Gly Gly Gly Thr Lys Leu Thr Val Leu Gly Gln Ser Lys Ala Ala Pro
                245                 250                 255

Ser Val Thr Leu Phe Pro Pro Ser Ala Ala Ala Ser Asp Lys Thr
            260                 265                 270

His Thr Cys Pro Pro Cys Pro Ala Pro Glu Leu Leu Gly Gly Pro Ser
            275                 280                 285

Val Phe Leu Phe Pro Pro Lys Pro Lys Asp Thr Leu Met Ile Ser Arg
        290                 295                 300

Thr Pro Glu Val Thr Cys Val Val Val Asp Val Ser His Glu Asp Pro
305                 310                 315                 320

Glu Val Lys Phe Asn Trp Tyr Val Asp Gly Val Glu Val His Asn Ala
                325                 330                 335

Lys Thr Lys Pro Arg Glu Glu Gln Tyr Asn Ser Thr Tyr Arg Val Val
            340                 345                 350

Ser Val Leu Thr Val Leu His Gln Asp Trp Leu Asn Gly Lys Glu Tyr
            355                 360                 365

Lys Cys Lys Val Ser Asn Lys Ala Leu Pro Ala Pro Ile Glu Lys Thr
        370                 375                 380

Ile Ser Lys Ala Lys Gly Gln Pro Arg Glu Pro Gln Val Tyr Thr Leu
385                 390                 395                 400
```

-continued

```
Pro Pro Ser Arg Glu Glu Val Thr Lys Asn Gln Val Ser Leu Thr Cys
            405                 410                 415

Leu Val Lys Gly Phe Tyr Pro Ser Asp Ile Ala Val Glu Trp Glu Ser
            420                 425                 430

Asn Gly Gln Pro Glu Asn Asn Tyr Lys Thr Thr Pro Pro Val Leu Asp
        435                 440                 445

Ser Asp Gly Ser Phe Phe Leu Tyr Ser Lys Leu Thr Val Asp Lys Ser
        450                 455                 460

Arg Trp Gln Gln Gly Asn Val Phe Ser Cys Ser Val Met His Glu Ala
465                 470                 475                 480

Leu His Asn His Tyr Thr Gln Lys Ser Leu Ser Leu Ser Pro Gly Lys
                485                 490                 495
```

```
<210> SEQ ID NO 25
<211> LENGTH: 808
<212> TYPE: DNA
<213> ORGANISM: Artificial sequence
<220> FEATURE:
<223> OTHER INFORMATION: antibody

<400> SEQUENCE: 25
ccatggccca ggtccagctg gtgcagtctg gggctgaggt gaagaagcct ggggcctcag      60
tgaaggtctc ctgcaaggtt tccggataca ccctcactga attatccatg cactgggtgc     120
gccagactcc tggaaaaggg cttgagtgga tgggaggttt tgatcctgaa gatggtgaaa     180
caatctacgc acagaagttc cagggcagag tcaccatgac cgaggacaca tctacagaca     240
cagcctacat ggagctgagc agcctgaggt ctgaggacac ggccgtgtat tactgtgcaa     300
cccaaggata tagtggctac gattactact ttgactactg gggccaggga accctggtca     360
ccgtctcctc agggagtgca tccgccccaa agcttgaaga aggtgaattt tcagaagcac     420
gcgtatcttc tgagctgact caggaccctg ctgtgtctgt ggccttggga cagacagtca     480
ggatcacatg ccaaggagac agcctcagaa gctattatgc aagctggtac cagcagaagc     540
caggacaggc ccctgtagtt gtcatctatg gtaaaaacga ccggccctca gggatcccag     600
accgattctc tggctccagc tcaggaaaca cagcttcctt gaccatcact ggggctcagg     660
cggaagatga ggctgactat tactgtaact cccgggacag cagtggtaac catcatgtgg     720
tattcggcgg aggaccaag ctgaccgtcc taggtcagcc caaggctgcc ccctcggtca     780
ctctgttccc accgtcctct gcggccgc                                        808
```

```
<210> SEQ ID NO 26
<211> LENGTH: 497
<212> TYPE: PRT
<213> ORGANISM: Artificial sequence
<220> FEATURE:
<223> OTHER INFORMATION: antibody

<400> SEQUENCE: 26

Met Ala Gln Val Gln Leu Val Gln Ser Gly Ala Glu Val Lys Lys Pro
1               5                   10                  15

Gly Ala Ser Val Lys Val Ser Cys Lys Val Ser Gly Tyr Thr Leu Thr
            20                  25                  30

Glu Leu Ser Met His Trp Val Arg Gln Thr Pro Gly Lys Gly Leu Glu
        35                  40                  45

Trp Met Gly Gly Phe Asp Pro Glu Asp Gly Glu Thr Ile Tyr Ala Gln
    50                  55                  60
```

-continued

```
Lys Phe Gln Gly Arg Val Thr Met Thr Glu Asp Thr Ser Thr Asp Thr
65                  70                  75                  80

Ala Tyr Met Glu Leu Ser Ser Leu Arg Ser Glu Asp Thr Ala Val Tyr
                85                  90                  95

Tyr Cys Ala Thr Gln Gly Tyr Ser Gly Tyr Asp Tyr Tyr Phe Asp Tyr
            100                 105                 110

Trp Gly Gln Gly Thr Leu Val Thr Val Ser Ser Gly Ser Ala Ser Ala
            115                 120                 125

Pro Lys Leu Glu Glu Gly Glu Phe Ser Glu Ala Arg Val Ser Ser Glu
        130                 135                 140

Leu Thr Gln Asp Pro Ala Val Ser Val Ala Leu Gly Gln Thr Val Arg
145                 150                 155                 160

Ile Thr Cys Gln Gly Asp Ser Leu Arg Ser Tyr Tyr Ala Ser Trp Tyr
                165                 170                 175

Gln Gln Lys Pro Gly Gln Ala Pro Val Val Val Ile Tyr Gly Lys Asn
            180                 185                 190

Asp Arg Pro Ser Gly Ile Pro Asp Arg Phe Ser Gly Ser Ser Ser Gly
            195                 200                 205

Asn Thr Ala Ser Leu Thr Ile Thr Gly Ala Gln Ala Glu Asp Glu Ala
        210                 215                 220

Asp Tyr Tyr Cys Asn Ser Arg Asp Ser Ser Gly Asn His His Val Val
225                 230                 235                 240

Phe Gly Gly Gly Thr Lys Leu Thr Val Leu Gly Gln Pro Lys Ala Ala
                245                 250                 255

Pro Ser Val Thr Leu Phe Pro Pro Ser Ser Ala Ala Ala Ser Asp Lys
            260                 265                 270

Thr His Thr Cys Pro Pro Cys Pro Ala Pro Glu Leu Leu Gly Gly Pro
            275                 280                 285

Ser Val Phe Leu Phe Pro Pro Lys Pro Lys Asp Thr Leu Met Ile Ser
        290                 295                 300

Arg Thr Pro Glu Val Thr Cys Val Val Val Asp Val Ser His Glu Asp
305                 310                 315                 320

Pro Glu Val Lys Phe Asn Trp Tyr Val Asp Gly Val Glu Val His Asn
                325                 330                 335

Ala Lys Thr Lys Pro Arg Glu Glu Gln Tyr Asn Ser Thr Tyr Arg Val
            340                 345                 350

Val Ser Val Leu Thr Val Leu His Gln Asp Trp Leu Asn Gly Lys Glu
            355                 360                 365

Tyr Lys Cys Lys Val Ser Asn Lys Ala Leu Pro Ala Pro Ile Glu Lys
        370                 375                 380

Thr Ile Ser Lys Ala Lys Gly Gln Pro Arg Glu Pro Gln Val Tyr Thr
385                 390                 395                 400

Leu Pro Pro Ser Arg Glu Glu Val Thr Lys Asn Gln Val Ser Leu Thr
                405                 410                 415

Cys Leu Val Lys Gly Phe Tyr Pro Ser Asp Ile Ala Val Glu Trp Glu
            420                 425                 430

Ser Asn Gly Gln Pro Glu Asn Asn Tyr Lys Thr Thr Pro Pro Val Leu
            435                 440                 445

Asp Ser Asp Gly Ser Phe Phe Leu Tyr Ser Lys Leu Thr Val Asp Lys
        450                 455                 460
```

-continued

```
Ser Arg Trp Gln Gln Gly Asn Val Phe Ser Cys Ser Val Met His Glu
465             470             475             480

Ala Leu His Asn His Tyr Thr Gln Lys Ser Leu Ser Leu Ser Pro Gly
            485             490             495

Lys
```